United States Patent
Prywes (12)

(10) Patent No.: US 6,264,668 B1
(45) Date of Patent: Jul. 24, 2001

(54) OPHTHALMOLOGIC INSTRUMENT FOR PRODUCING A FISTULA IN THE SCLERA

(76) Inventor: Arnold S. Prywes, 4212 Hempstead Turnpike, Bethpage, NY (US) 11714

( * ) Notice: Subject to any disclaimer, the term of this patent is extended or adjusted under 35 U.S.C. 154(b) by 0 days.

(21) Appl. No.: 09/154,394

(22) Filed: Sep. 16, 1998

(51) Int. Cl.[7] .................................................. A61B 17/32
(52) U.S. Cl. ........................ 606/167; 606/166; 606/184; 606/4; 600/567
(58) Field of Search ..................................... 606/166–167, 606/15, 107, 183–186, 4, 5, 6; 30/304, 299, 279.2, 305; 604/9.22; 128/305; 600/567, 564

(56) References Cited

U.S. PATENT DOCUMENTS

| | | | |
|---|---|---|---|
| 3,007,471 | * | 11/1961 | McClure, Jr. .......................... 600/567 |
| 4,578,865 | * | 4/1986 | Keller ...................................... 30/304 |
| 4,649,919 | * | 3/1987 | Thimsen et al. ......................... 604/22 |
| 4,651,752 | * | 3/1987 | Fuerst ..................................... 600/567 |
| 4,696,298 | * | 9/1987 | Higgins et al. ......................... 128/305 |
| 5,047,008 | * | 9/1991 | De Juan, Jr. et al. .................. 604/22 |
| 5,201,747 | * | 4/1993 | Mastel ..................................... 606/167 |
| 5,222,959 | * | 6/1993 | Anis ........................................ 606/107 |
| 5,224,950 | | 7/1993 | Prywes . |
| 5,478,338 | * | 12/1995 | Reynard .................................. 606/15 |
| 5,487,747 | * | 1/1996 | Stagmann et al. ..................... 606/166 |
| 5,549,622 | * | 8/1996 | Ingram .................................... 606/167 |
| 5,571,127 | * | 11/1996 | DeCampli .............................. 606/167 |
| 5,628,760 | * | 5/1997 | Knoepfler .............................. 606/167 |
| 5,741,245 | * | 4/1998 | Cozean et al. ............................ 606/5 |
| 5,752,967 | * | 5/1998 | Kritzinger et al. .................... 606/167 |
| 5,788,667 | * | 8/1998 | Stoller .................................... 606/167 |
| 5,797,937 | * | 8/1998 | Ichikawa et al. ..................... 606/167 |
| 5,817,115 | * | 10/1998 | Nigam ................................... 606/167 |
| 6,007,511 | * | 12/1999 | Prywes ...................................... 604/9 |

* cited by examiner

Primary Examiner—Michael H. Thaler
Assistant Examiner—Julian W. Woo
(74) Attorney, Agent, or Firm—Ladas & Parry

(57) ABSTRACT

An instrument for producing a fistula through a tissue wall of an eye of a patient. The instrument has a housing with a flat blade supported in the housing for penetrating through the tissue wall to form an incised slit in the wall forming a tunnel therein. By rotating the housing and the flat blade a lamellar flap can be formed at the top of the tunnel. The housing contains a second cutting device to remove a large portion of tissue material at the bottom of the tunnel producing an aperture joined to the slit for forming the fistula. The cutting device can be a curved blade having a scoop-shaped cross-section, a punch or an optical fiber capable of transmitting a laser beam. The cutting device is operated while the flat blade remains in the tunnel.

19 Claims, 28 Drawing Sheets

OPHTHALMOLOGIC INSTRUMENT FOR PRODUCING A FISTULA IN THE SCLERA

FIELD OF THE INVENTION

The invention relates to an instrument for producing a fistula in a tissue wall of a patient, and more particularly to a fistula in the sclera in the eye of the patient. The instrument is denoted as a trabeculectomy probe.

The instrument is applicable to the formation of such a fistula to relieve intraocular pressure in the anterior chamber of the eye of a patient suffering from glaucoma.

BACKGROUND

Glaucoma is a disease where the intraocular pressure is elevated. It affects significant numbers of our population. The treatment of glaucoma is usually medical, however, medications often fail to control some forms of glaucoma. When further treatment is required a microsurgical operative procedure is performed. This procedure involves constructing a fistula or opening in the tissue wall of the sclera to enhance fluid flow from the internal portion of the eye (ciliary body) which secretes the fluid (aqueous humor) through the newly formed opening. This opening is typically made in a cutting type of procedure. This involves incising the external ocular tissues (conjunctiva) and dissecting the scleral tissues. This dissection results in attendant risks including bleeding, and development of extremely low intraocular pressure or hypotony. Post operative care is prolonged due to the large size of the scleral incisions, the possibility of complications and variability in wound healing. The procedure is generally referred to as a filtering operation, as a trabeculectomy, sclerectomy or lamellar scleral flap procedure. In a so-called full thickness fistulization procedure, a hole of a diameter of 2–4 mm is formed through the sclera. In a so-called partial thickness fistulization, an opening in the form of a slit of 100–300 microns extends through the tissue wall into the anterior chamber and an ostium or aperture of 2–4 mm extends from the slit at the posterior surface of the tissue wall. The trabeculectomy, partial thickness sclerectomy or fistulization, has become the prevalent procedure since a valve effect occurs when a partial thickness aperture is present. Many of the immediate post operative complications of surgery are reduced by the more controlled outflow achieved by this type of surgery.

Recently, lasers have been used to perform fistulizing procedures. These laser procedures are currently used to produce a full thickness fistula by a procedure referred to as laser sclerostomy. This has been performed with holmium, YAG, erbium and other laser penetrating means. In the current mode, (ab externo), a small incision is made after a subconjunctival injection of air or other fluid has been introduced into the subconjunctival space. This fluid allows the laser probe to pass beneath the conjunctival tissue without "button-holing" the tissue. The laser probe is then introduced into the subconjunctival space. The probe is advanced to the sclera proximal to the limbal area of the eye. The laser energy is directed from the laser probe toward the sclera until the energy produces a fistula through the full thickness of the sclera. Once this occurs the laser probe is removed and the initial conjunctival incision is sutured and the procedure is complete.

In the ab interno version of filtering surgery, laser energy is aimed using a contact lens (goniolens) to produce a full thickness opening in the sclera. A mechanical method of producing a fistula using a rotating, cutting blade (trabecuphine) also results in a full thickness opening.

The ab interno fistulizing surgery, by lasers or cutting, suffers, in its present state, from several disadvantages. Ab externo laser surgery has produced only full thickness fistulas. This results in attendant problems with hypotony, choroidal effusion, choroidal hemorrhage and shallowing of the anterior chamber of the eye. The fistula also frequently closes. Modifications of the procedure employ either intra-operative or post-operative injections of anti-scarring agents (antimetabolites) to improve the results. The small size of the fistula (100–300 microns) may be an advantage for controlling fluid flow, but the long term success of such small fistulas may be temporary since they scar down more easily than the larger (2–4 mm) fistulas in guarded filtering surgery (trabeculectomy) by cutting. Larger fistulas in a full thickness procedure (sclerectomy, thermal sclerostomy) produce a greater frequency of complications than guarded procedures.

SUMMARY OF THE INVENTION

The invention addresses the problems of producing a partial thickness fistula, with and without separate conjunctival injections, or post operative injections. The invention provides an instrument to produce a controlled outflow fistula (trabeculectomy). It allows the surgeon to use the same instrument to produce a lamellar scleral flap and a partial thickness fistula without requiring the sequential use of separate cutting implements. The scleral flap is created and made of the proper depth without the use of a forceps. No suturing of a trabeculectomy flap is necessary. The use of adjunctive antimetabolites (Mitomycin C. etc.) is given intra-operatively transconjunctivally prior to the introduction of the instrument in the ab interno and ab externo methods, and through the operative conjunctival incision in the ab externo method.

The instrument may be used in the ab interno or ab externo modes. In one embodiment using an external sub-conjunctival approach, irrigation into and aspiration out of the wound of antimetabolites or other fluids, such as viscoelastics which elevate the subconjunctival space prior to the introduction of the instrument may be employed.

The invention provides an instrument which is a multi-function device that simplifies the procedure which presently requires a larger wound, multiple instruments and an operating room with anesthesia. This simplified procedure may be performed with topical anesthesia alone in an ophthalmologist's office. It may be possible for tissue glues to be used to close the small incision without sutures in the ab externo technique. The ab interno technique is performed using a corneal incision (paracentesis) which is made in a self-sealing fashion, requiring no sutures for wound closure.

The instrument according to the invention is referred to as a trabeculectomy probe, comprises a housing, a blade supported in said housing for extending from the housing to penetrate the tissue wall of a patient and produce an incised slit in said tissue wall forming an opening or tunnel therein. The blade can be utilized to form a scleral flap at the anterior surface of the tissue wall. The housing additionally carries a fistula-forming means for entering said slit, while the blade remains in the slit, to excise tissue from a posterior portion of said wall which bounds the slit to produce an ostium or opening at the posterior surface of the tissue wall to complete the fistula in said tissue wall.

The fistula-forming means can be a laser generating means for producing a tissue-cutting laser beam, or a second blade or a punch.

The probe may further include irrigation and aspiration channels which have respective separate ports connectable to irrigation and aspiration sources.

In the ab interno mode using a second blade as the fistula-forming means, a subconjunctival injection is used to elevate the conjunctiva to avoid penetration of the conjunctiva by the blade penetrating the sclera. The housing is introduced through a corneal incision. The first blade is flat and makes the corneal incision as well as the scleral incision, distal to the corneal incision, to form the opening in the tissue wall as a through slit. The second blade is curved and shaped as a scoop and is displaceable relative to the first blade to be fully advanced to press against an opposed, flat, non-cutting undersurface of the first blade. When fully advanced, the scoop-shaped blade excises a defined section of the sclera or the trabecular meshwork at the posterior surface of the tissue wall to form the ostium. When the probe is removed, the procedure is complete.

In the ab externo mode, the flat blade initially enters the subconjunctival space after making a small stab incision in the conjunctiva at a distance from the limbus of the eye. The flat blade is advanced under a pocket of fluid (air or liquid). This fluid is introduced at the time of the stab incision through the irrigation channel provided in the housing. The fluid is injected to avoid inadvertent buttonhole incisions of the conjunctiva. The flat blade may have marking means thereon to indicate depth of penetration of the blade into the sclera. The flat blade incises the sclera at the proper distance from the limbus to form a slit through the sclera with anterior and posterior wall portions of the sclera bounding the slit. The incised sclera is fashioned into the "pocket" configuration by incising the anterior wall portion through to the slit thus forming a flap above the slit, referred to as a scleral flap. The scoop-shaped blade is then advanced into the pocket by manually displacing the scoop shaped blade. Slight elevation or tilting of the flat blade enlarges the pocket and facilitates the entry of the scoop-shaped blade into the pocket. The flat blade elevates the scleral flap formed at the top of the pocket, without a forceps, by lifting the entire probe, thereby allowing the scoop-shaped blade to be introduced into the scleral pocket. Once the scoop-shaped blade is advanced into the pocket created by the flat blade, the scleral lamellar excision is completed. Removal of the probe removes the excised tissue which may be submitted for tissue diagnosis. The length and width of the flat blade and the scoop-shaped blade may be variable in size and shape. In one embodiment, the flat blade is fixed to the housing which is in the form of a cannula which contains irrigation and aspiration channels and, optionally, an optical fiber for delivery of laser energy. The optical fiber can be fixed or it can be movable so as to be advanced from within the cannula, for cautery if necessary. The flat blade remains stationary, while the scoop-shaped blade can be advanced and retracted.

In another embodiment, the blades may both be retractable and removable from the housing for allowing the blades to be sharpened or replaced. Various interchangeable blades with different functions may be introduced within the housing. The housing may contain a separate removable sleeve containing the blades, the optical laser fiber and the aspirating and irrigation channels. The length and width of the blades are determined by the nature of the incision desired. A pocket having a three sided flap can be created by using side cutting portions of the flat blade, the flap being made by slightly elevating and rotating the blade in opposite direction. A two sided flap is made by rotating the blade in only one direction. When forming the ostium at the posterior surface of the tissue wall, the flat blade lifts the scleral flap allowing the curved, scoop-shaped blade to be advanced into the scleral pocket. No forceps is required to lift the scleral flap to allow the curved, scoop-shaped blade access into the scleral pocket. The flat blade is constructed to produce an incision to a prescribed depth without a forceps and allows the flap of the scleral pocket to be lifted simultaneously. The flat blade eliminates the need for using a scissors to cut the sides of the scleral pocket to form the flap. The curved, scoop-shaped blade eliminates the need for removing the material at the posterior surface of the tissue wall with a separate punch or with scissors and forceps. The curved, scoop-shaped blade is introduced and held at the proper angle to allow tissue removal without the use of separate surgical instruments.

The probe may be constructed with variable dimensions at the tip of the blade to allow for larger or smaller openings for the scleral incision. A set of probes with different housing dimensions and blade sizes may be provided for larger or smaller filtration fistulas. The blades or the entire probe may be reusable or disposable. The blades may be constructed of metal, gem, ceramic, plastic, polymer or other rigid material capable of being sharpened. The housing may be made of metal, polymer, plastic or similar rigid or flexible material.

In one embodiment, the probe is constructed with a modular connector which connects the probe to various types of tools such as laser generators, irrigators, aspirators, etc. One or several laser conducting materials can transmit the laser energy. The ports of the irrigation and aspiration channels are connected to flexible tubings. A manual or automated irrigation and aspiration system module conducts fluid. A simple manual method (syringe) is employed to inject fluid into or aspirate fluid from the subconjunctival space. The irrigation and aspiration module connects to the laser transmission module (optical fibers). In another embodiment, the laser and irrigation and aspiration modules are separate. A means for advancing the housing can be provided which may be manual or automated.

When the instrument is utilized with the tissue-cutting means constructed as a laser generator, an optical fiber for transmitting a laser beam extends in the housing adjacent to the flat blade. The laser beam serves to produce a partial thickness fistula in the tissue wall after the flat blade has formed the slit opening therein.

When the tissue-cutting means comprises a punch, this is mounted adjacent to the flat blade and serves to produce the partial thickness fistula after the flat blade has formed the slit opening in the wall.

Advantages and Novel Aspects of the Invention

Known sclerostomy (scleral hole-forming) means produce a large hole through the full thickness of the sclera. The instrument of the invention produces a partial thickness opening i.e. a large hole through only a portion of the thickness of the tissue wall.

Previous sclerostomy (scleral hole-forming) means have employed laser probes. The instrument of the invention utilizes a cutting blade with further cutting means (blade or punch) or laser beam generating means in combination within a housing and with means for manual or automated irrigation and aspiration.

Previous sclerostomy (scleral hole-forming) means require a separate conjunctival injection prior to insertion of the probe. In the ab externo method, the instrument of the invention injects the fluid concurrently with the introduction of the probe.

Previous sclerostomy (scleral hole-forming) means required the use of a punch or scissors to remove tissue. The instrument of the invention employs two separate blades within a small cannula to excise the tissue.

Previous sclerostomy (scleral hole-forming) means required a separate instrument (scissors or blade) to incise the conjunctiva. The instrument of the invention uses the flat blade thereof to make this incision.

Previous sclerostomy (scleral hole-forming) means require that introduction of fluid into the subconjunctival space be performed with a separate infusing cannula or needle. The instrument of the invention uses the irrigation means in the instrument to accomplish this.

Previous glaucoma procedures with cutting instruments utilize separate means for hemostasis. The instrument of the invention uses the cauterizing means in the instrument for hemostasis.

Conventional blades with markings for incising the sclera have not been associated in a common instrument with both irrigation and aspiration means. The instrument of the invention uses blades which are marked and associated with both irrigation and aspiration means.

Previous sclerostomy (scleral hole-forming) means have no integrated, enclosed blades associated with the sclerostomy. The instrument of the invention has two blades, both of which may be fixed or retractable, with or without markings and which allow excision of tissue.

Previous sclerostomy (scleral hole-forming) means have probes with integral laser delivery systems without advancement or retraction of the optical, laser-transmitting fibers within a cannula. The instrument of the invention has integral means for retraction or advancement of the optical fibers.

Previous surgical trabeculectomies (in which an ostium is formed in the trabecular meshwork at the posterior surface of the sclera) require that a forceps be used to elevate the scleral flap to introduce a punch to remove scleral tissue or to introduce a scissors to excise a block of scleral tissue. The flat blade of the instrument of the invention lifts the scleral flap allowing the scoop-shaped blade or the punch to be advanced into the scleral pocket. No forceps is required to lift the scleral flap. Present surgical modalities do not allow these procedures to be performed without two instruments or two separate entries through the same wound.

Previous surgical trabeculectomies require that lifting of the flap and cutting the sclera require two instruments. The flat blade of the invention is constructed to produce an incision to the prescribed depth without a forceps and also to allow the flap of the scleral pocket to be lifted.

Previous surgical trabeculectomies require that a scissors be used to excise the trabecular meshwork. The flat blade eliminates the need for using a scissors to cut the sides of the scleral pocket and the scoop-shaped blade eliminates the need for separate instruments, such as a punch, scissors or forceps to remove the trabeculectomy specimen.

Previous surgical trabeculectomies require that the surgical punch, blade or scissors be placed at the proper angle to excise tissue. The instrument of the invention allows the scoop-shaped blade to be introduced and placed at the proper angle to allow tissue removal without the use of separate surgical instruments.

Previous surgical trabeculectomies require that two separate instruments were required to lift the sclera and incise it. An additional instrument is then required to lift the scleral flap to excise the trabecular meshwork. The instrument of the invention eliminates the use of multiple instruments and incises and lifts the sclera and introduces the scoop-shaped blade or punch to remove the tissue completing the partial thickness fistula and to enable biopsy of tissue. A laser can also perform the removal of tissue but without obtaining a tissue sample for biopsy.

Previous surgical trabeculectomies had no mechanism for visualizing the surgery endoscopically. The device of the invention is capable of including a light pipe and video camera to visualize the size and patency of the fistula while it is being formed by the laser beam, the scoop-shaped blade or the punch.

The instrument of the invention allows excisional biopsies of tissues to be performed with a limited incisional height, width and depth.

DETAILED DESCRIPTION OF PREFERRED EMBODIMENTS

The invention will be described hereafter with reference to three embodiments thereof for producing so called partial thickness fistulas in the tissue wall of the sclera in ab externo and ab interno procedures. In the ab externo procedure, initial entry into the tissue wall is made from the subconjunctional space at the anterior surface of the tissue wall whereas in the ab interno procedure initial entry into the tissue wall is made from the anterior chamber at the posterior surface of the tissue wall.

The three embodiments each includes a flat blade for producing the initial entry incision and means for producing the ostium or aperture in the partial thickness of the tissue wall. The three respective embodiments of the means for producing the ostium are:

1. A cutting blade
2. A punch
3. A tissue-cutting laser beam.

First Embodiment with the Cutting Blade

Figure 1:
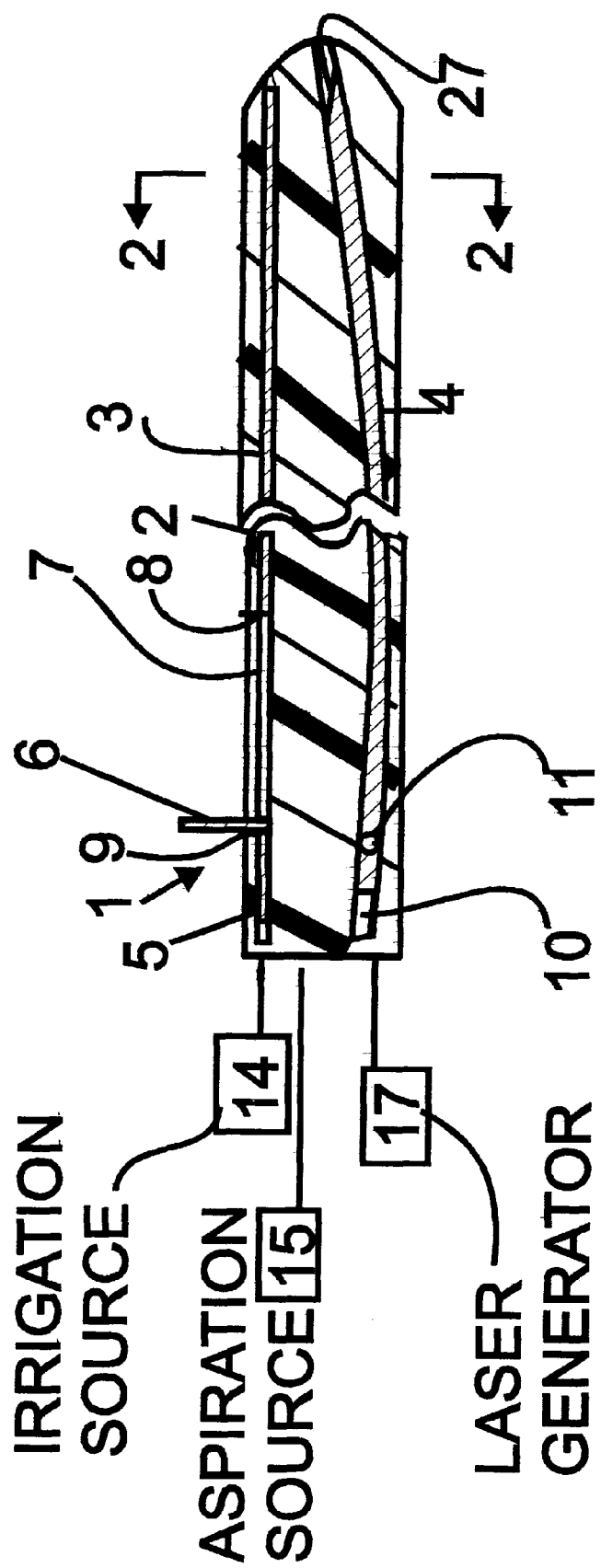
FIG. 1 is a longitudinal, cross-sectional view through one embodiment of the instrument according to the invention with the blades of the instrument retracted.
Figure 2:
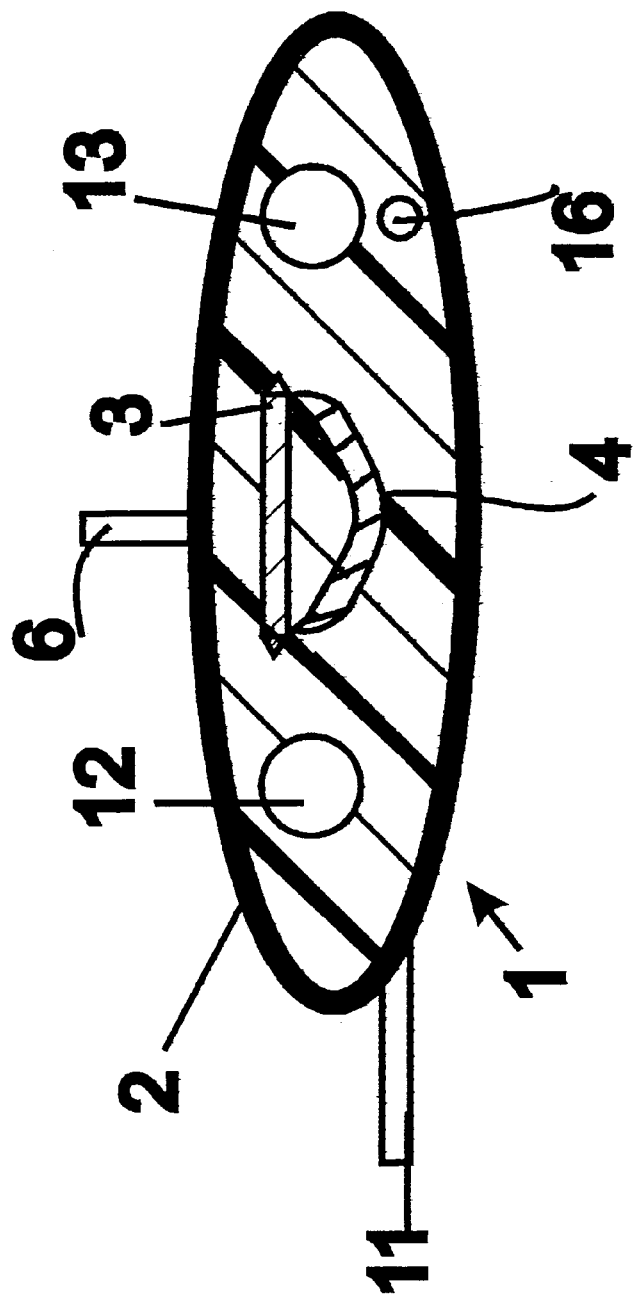
FIG. 2 is a transverse, cross-sectional view taken along line 2—2 in FIG. 1.

Referring to FIGS. 1 and 2 of the drawing, therein is seen an instrument or probe 1 which comprises a housing or cannula 2 made of a plastic material (or other rigid material such as metal, ceramic etc.) and generally elongated longitudinally and provided with a round cross-section, such as the elliptical cross-section shown in FIG. 2. The instrument 1 is illustrated on enlarged scale and has a maximum width along the major axis of the elliptical cross-section of less than 6 mm and preferably less than 4.5 mm, a maximum width along the minor axis of the elliptical cross-section of about 4 mm and an axial length of about 7 cm. The housing 2 can also have a circular cross section.

Figure 3:
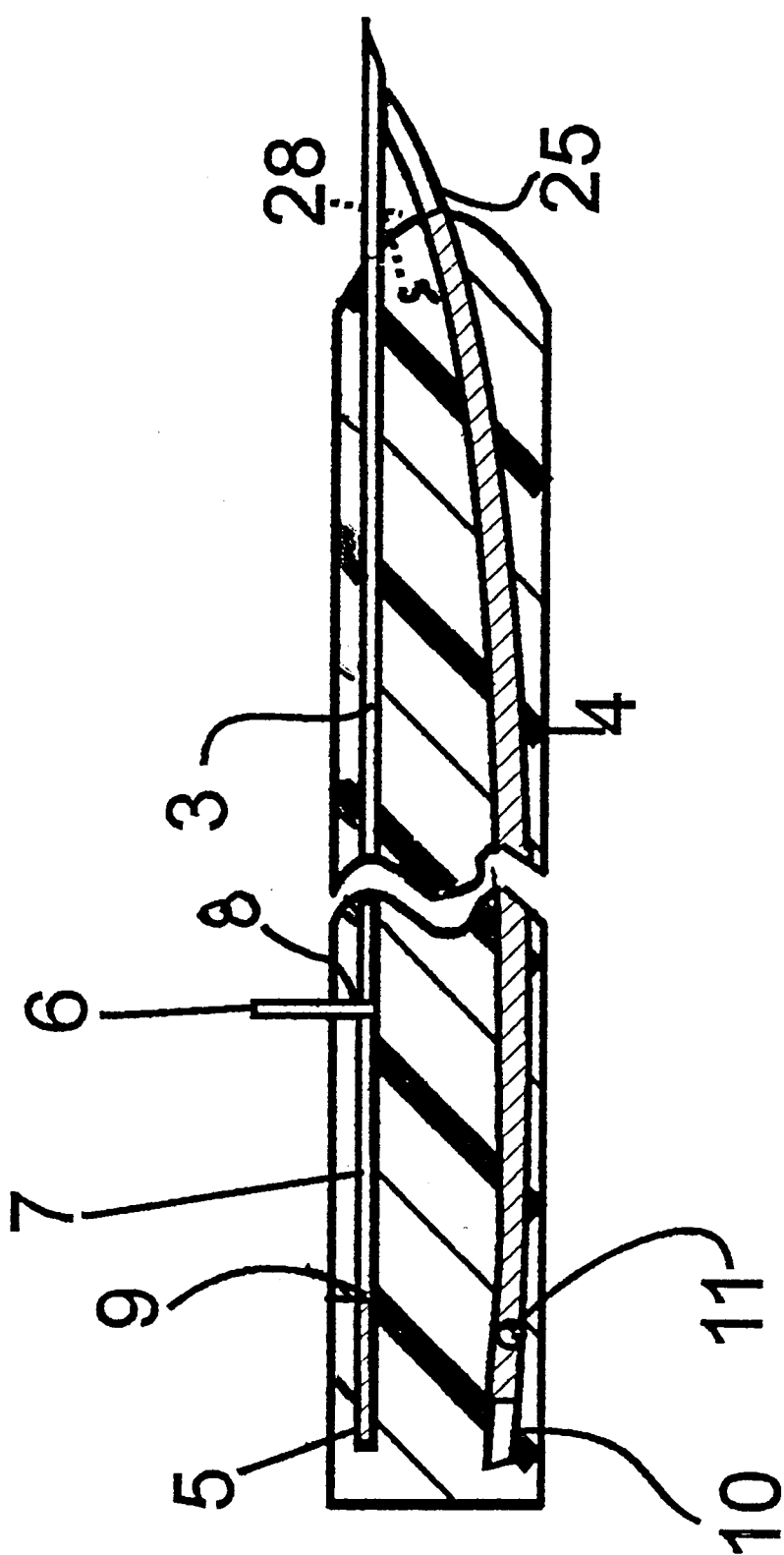
FIG. 3 shows the instrument of FIG. 1 with the blades thereof extended.

The housing 2 contains a first, flat cutting blade 3 in a superior position and a second, curved, cutting blade 4 in an inferior position below flat blade 3. The flat blade 3 is slidably supported for axial movement, in the plane of the blade, in a slot 5 in the housing 2 and the curved blade 3 is movable in a correspondingly curved slot 10 between a retracted position shown in FIG. 1 and an extended position shown in FIG. 3. The flat blade 3 has a width of 2.5 mm. A manually engageable lever 6 is fixed to blade 3 at its distal end and projects from the housing 2 through a narrow slot 7 therein for moving the blade 3 between its retracted and extended positions. The front and rear edges 8 and 9 of slot 7 serve as abutment surfaces for lever 6 to define the extended and retracted positions of blade 3. The curved blade 4 is slidably displaced in the curved slot 10 by engaging a lever 11 on blade 4 extending laterally outside the housing through a further curved slot therein (not shown). The curved blade 4 travels along a curved path defined by slot 10 and in its extended position as shown in FIG. 3, the curved blade 4 projects at an angle relative to the flat blade 3 and contacts the lower, non-cutting, surface thereof. The curved blade 4 has an arcuate cross section to confer a scoop-shape to the curved blade as shown in FIG. 2, the significance of which will become apparent later.

The housing 2 contains longitudinal channels 12, 13, laterally on opposite sides of the blades 3, 4, the channels extending through the housing for conveying fluid for irrigation and aspiration purposes. In this respect, channel 12 has a rear port adapted to be connected to an irrigation source 14 and channel 13 has a rear port adapted to be connected to an aspiration source 15. When the channels 12 and 13 are connected to their respective irrigation and aspiration sources, fluid can be supplied to and removed from openings of the channels at the front of the housing for purposes to be explained later. Suitable valve means (not shown) are manually operated by the surgeon to connect or disconnect the channels 12, 13 from their respective sources.

The housing 2 additionally contains an optic fiber 16 (FIG. 2) adapted for connection to a laser generator 17 for supplying laser energy at the front of the housing for various purposes, such as cauterizing wounds as will be explained later. The optic fiber 16 is supported for slidable movement in a respective slot (not shown) between a retracted inoperative position and an extended operative position in which the optic fiber extends from the housing. It is also possible for the optic fiber to be fixed in the housing in an operative position.

Figure 4:
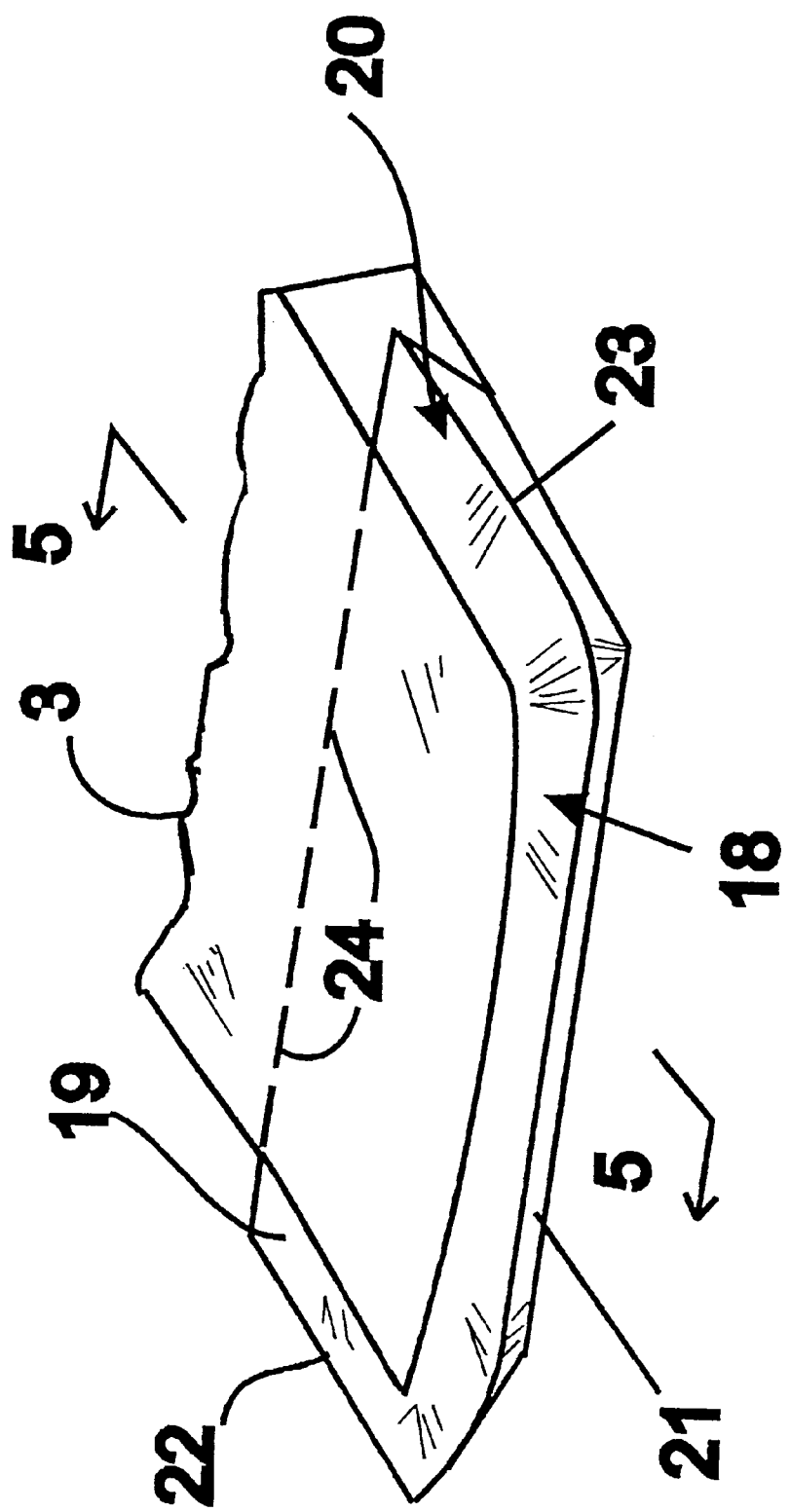
FIG. 4 is a perspective view of a portion of the flat blade of the instrument in FIG. 1.

Referring to FIG. 4, therein it is seen that flat blade 3 has a generally rectangular configuration with a rectilinear front portion 18 and parallel lateral side portions 19, 20. The flat blade 3 is intended to form a lamellar pocket or tunnel in a tissue wall of the eye of a patient, as will be explained more fully later. Instead of being rectilinear, the front portion can be curved or V-shaped. Various blade configurations are shown in my earlier U.S. Pat. No. 5,224,950 and are usable herein for the flat blade 3. The blade 3 is tapered in thickness at portions 18–20 to form respective cutting edges 21–23 so that when the blade 3 is inserted partially into a tissue wall, a pocket is formed therein whereas if the blade 3 is inserted completely through the tissue wall a slot or tunnel is formed in the tissue wall. As in U.S. Pat. No. 5,224,950, the blade 3 is provided with marking means 24 to indicate depth of penetration of the blade into the tissue wall.

Figure 7:
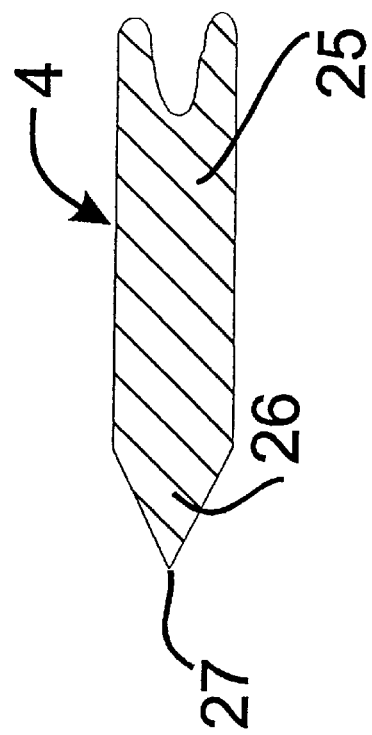
FIG. 7 is an enlarged, cross-sectional view taken on line 7—7 in FIG. 6.
Figure 5:
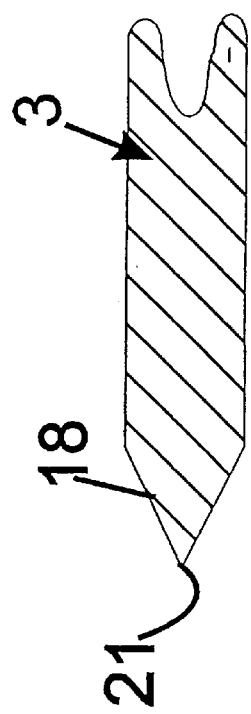
FIG. 5 is an enlarged, cross-sectional view taken along line 5—5 in FIG. 4.
Figure 6:
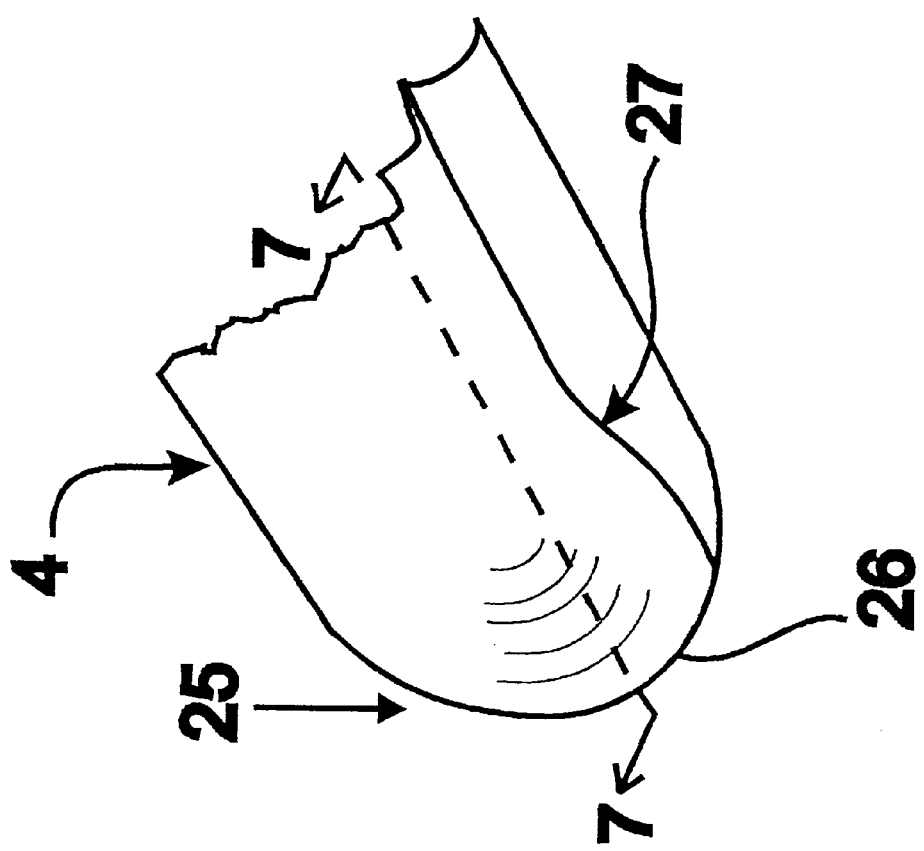
FIG. 6 is a diagrammatic, perspective view of a front portion of a scoop-shaped blade of the instrument in FIG. 1.
Figure 8:
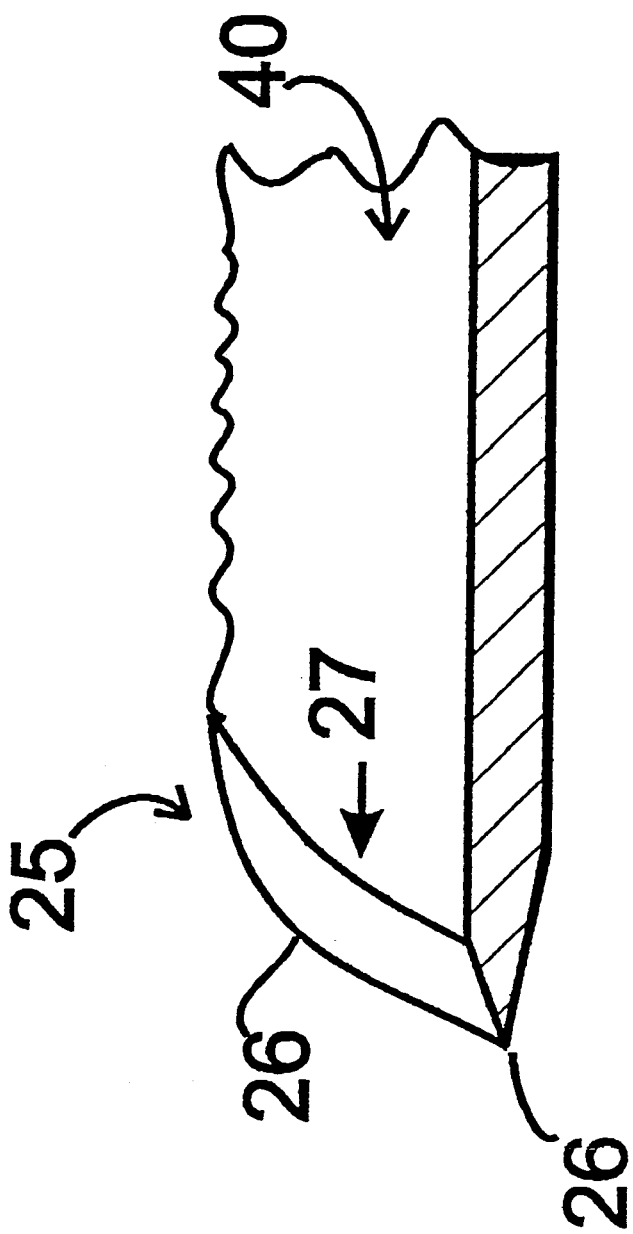
FIG. 8 is a perspective view from above, on enlarged scale, of a portion of the blade shown in FIG. 7.

The front portion 25 (FIG. 7) of curved, blade 4 has portions 26 at its front and lateral sides which are tapered to form cutting edges 27 in FIGS. 6 and 7 to gouge out tissue from the tissue wall as will be explained later. The edges 27 are inclined (See FIGS. 6 and 8) in order to mate with the lower surface of the flat blade 3 when blades 3 and 4 are extended as shown in FIG. 3 to enclose a wedge-shaped space 28.

The instrument or probe 1 is used as follows.

The instrument 1 can be utilized in the ab interno or ab externo operations to achieve a partial thickness fistulization. In the ab interno operation, the instrument proceeds at the posterior surface of the tissue wall from within the anterior chamber of the eye whereas in the ab externo operation, the instrument proceeds from the anterior surface of the tissue wall.

Figure 9:
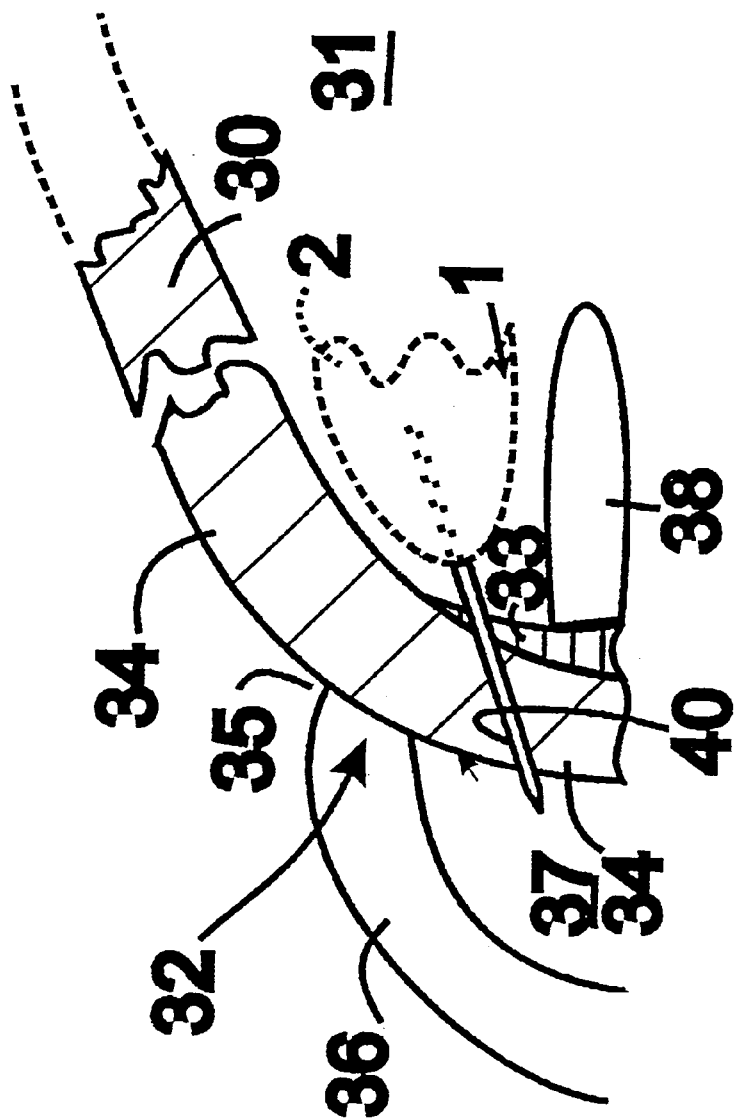
FIG. 9 is a diagrammatic sectional view showing use of the instrument in an ab interno operation in a first stage thereof.

Referring to FIG. 9, herein is seen the first stage in the ab interno operation. Therein, the instrument 1 has been introduced through the cornea 30 via a paracentesis or incision made by the flat blade 3 using the sharp cutting edges 21–23. The cutting edges 21–23 pierce the cornea 30 and continue across the anterior chamber 31 to penetrate through and incise the full thickness of the tissue wall 32 in the region where the trabecular meshwork 33 is formed at the posterior surface of the sclera 34. The instrument is advanced to a position with blade 3 extended, so that the marking means 24 on the blade 3 indicates the limit depth of penetration. The blade 3 forms a slit or tunnel 40 completely through the tissue wall. Visible in FIG. 9 is the corneal limbus 35 and the conjunctiva 36. Prior to the incising of the sclera, an injection of a viscoelastic fluid is made beneath the conjunctiva 36 to elevate the conjunctiva from the sclera and expand the subconjunctival space 37 to prevent the blade 3 from penetrating the conjunctiva 36. Also visible in FIG. 9 is the iris 38 of the eye.

Figure 10:
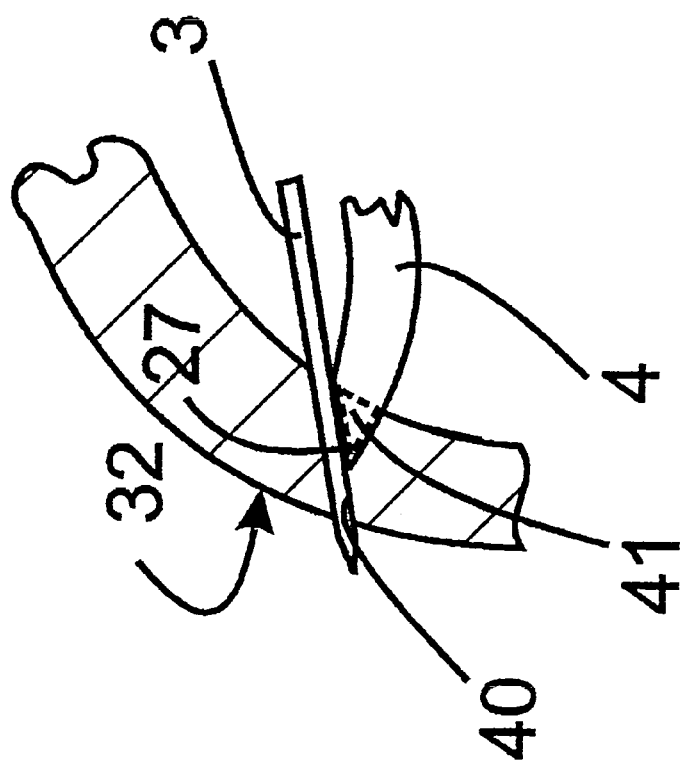
FIG. 10 shows the instrument in a second stage of the ab interno operation.
Figure 11:
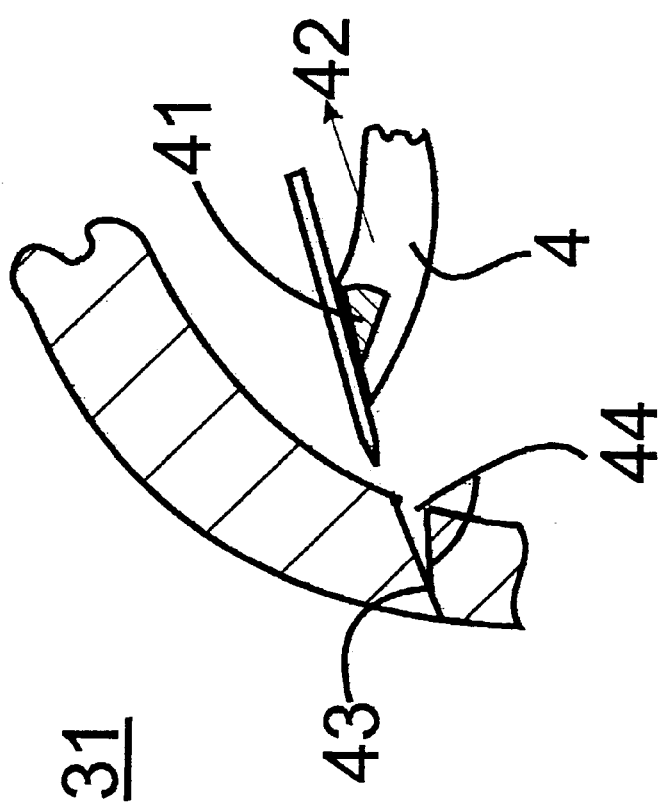
FIG. 11 shows the instrument in a third stage of the ab interno operation.
Figure 12:
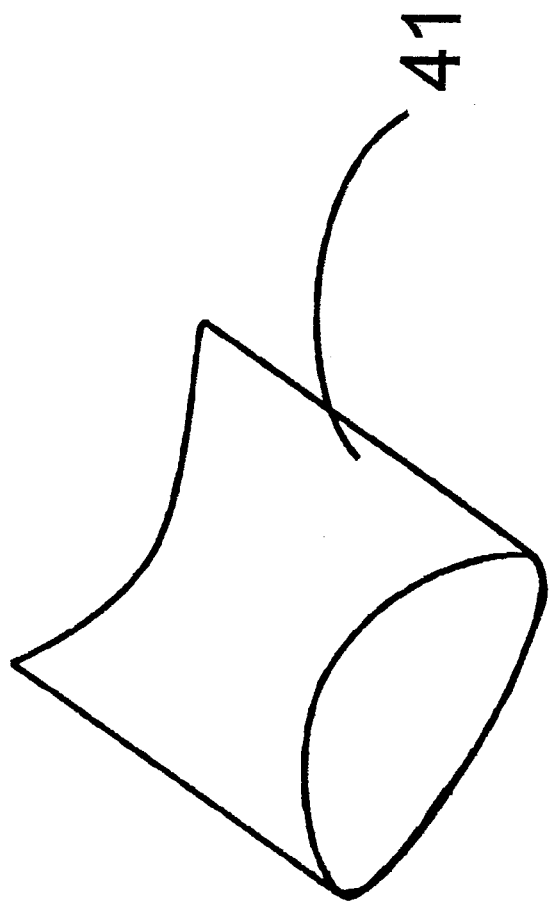
FIG. 12 is a perspective view showing a wedge of tissue excised by the instrument in the third stage.

As shown in FIG. 10, while the flat blade 3 remains in the incision in the tissue wall 32, the curved blade 4 is advanced and the cutting edges 26 at the front end of the scoop-shaped blade gouge out and excise a wedge-shaped portion 41 of the posterior wall portion (mainly trabecular meshwork) of the tissue wall. The instrument 1 is then retracted in the direction of arrow 42 with the blades 3 and 4 in the extended positions as shown in FIG. 11. The excised portion 41 is removed intact with the blades to produce a trabeculectomy in the tissue wall in which a thin slit 43, formed by the flat blade, extends completely through the wall and an ostium or opening 44 of greater size, produced by removal of wedge-shaped portion 41, extends through a portion of the wall thickness. The wedge-shaped portion 41 can be investigated, for example, by biopsy techniques.

During the procedure, the irrigation and aspiration channels 12 and 13 can be utilized as desired for supplying fluids, such as a balanced salt solution, anti-inflammatory agents and for aspirating fluids and loose cut tissue materials. The laser generator 17 and optic fiber 16 can be used to produce laser beams for cautery purposes.

In the ab externo operation, the instrument is used as described for the ab interno operation except that instead of proceeding from within the anterior chamber outwardly, the instrument proceeds externally towards the anterior chamber. The ab externo procedure will be described in detail later with reference to FIGS. 25–29.

Second Embodiment with the Punch

Figure 13:
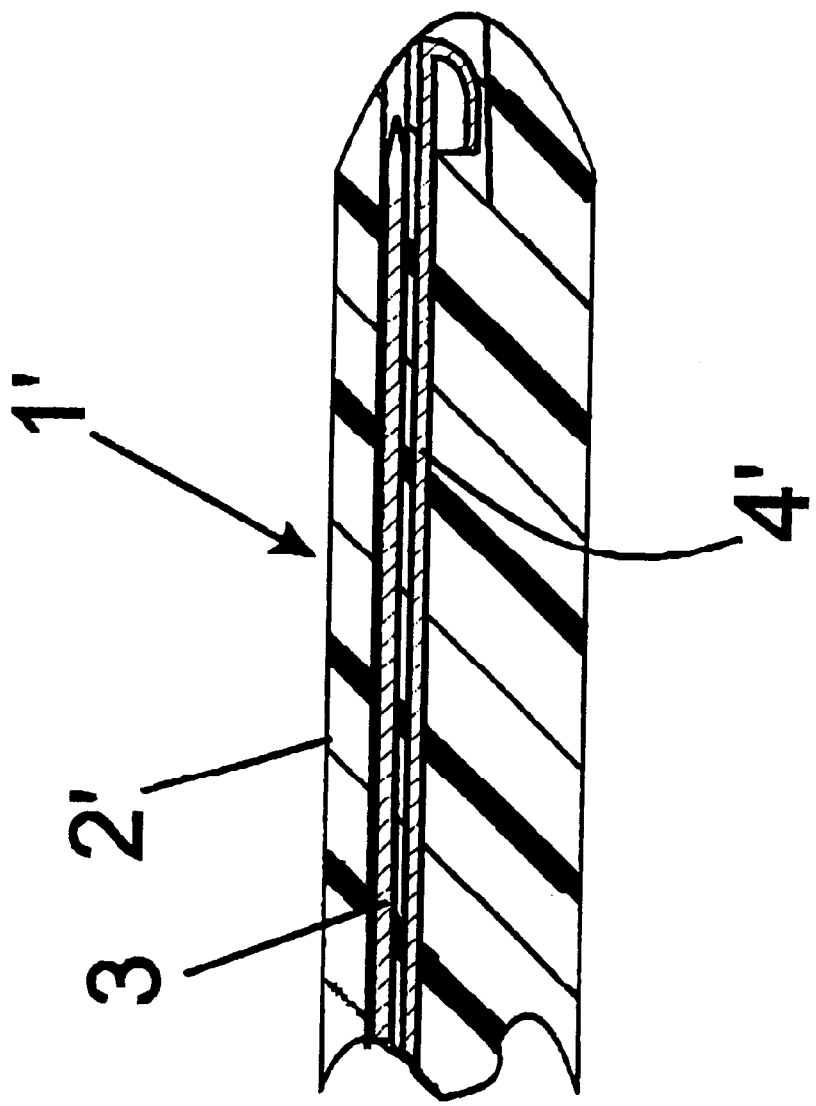
FIG. 13 is a longitudinal, cross-sectional view through a second embodiment of the instrument of the invention.
Figure 14:
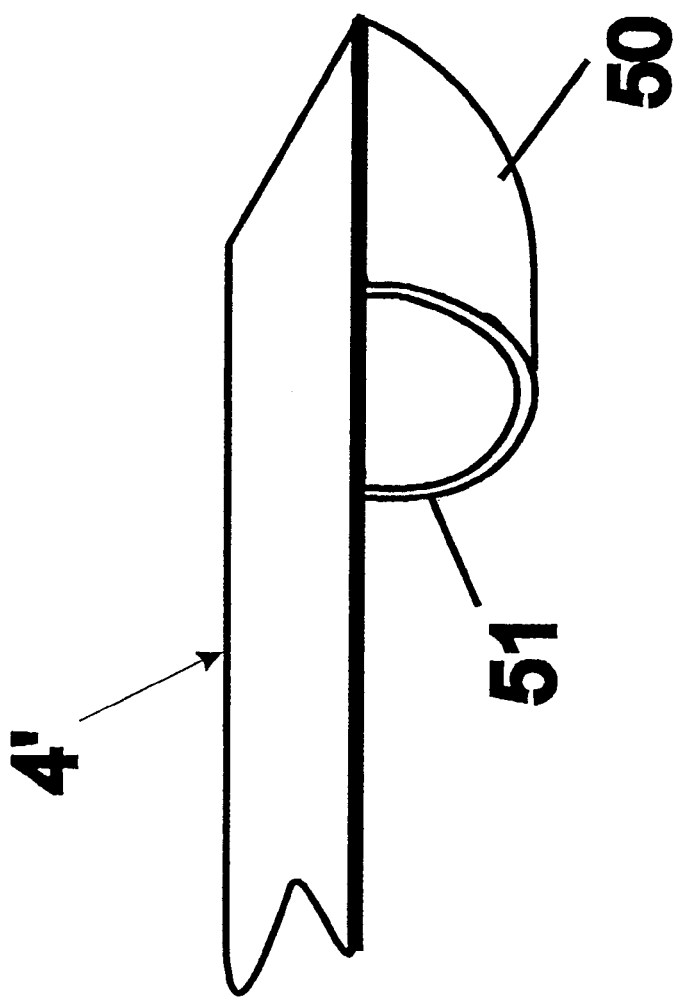
FIG. 14 is a perspective view diagrammatically illustrating a punch of the instrument of FIG. 13.

The second embodiment of the instrument has a number of elements common to those of the first embodiment and the same reference numerals will be used to designate these elements. Referring to FIG. 13, the second embodiment of the instrument is designated by 1' and is essentially distinguished from the embodiment of FIG. 1 by providing a punch 4' instead of the curved cutting blade 4. In the instrument 1', the flat blade 3 is constructed as in the first embodiment. The punch 4' is mounted beneath blade 3 for advancing and retracting movements substantially parallel to blade 3. The punch 4' is formed at its leading edge with a hollow bucket-shaped punch portion 50 which is closed at its leading edge and has a rearwardly facing perimetral edge portion 51 which tapers in thickness and forms a sharp cutting edge. The bucket-shaped punch portion can have a cross-section of U-shape as shown or of D-shape, or be ovoid or oblong.

Figure 15:
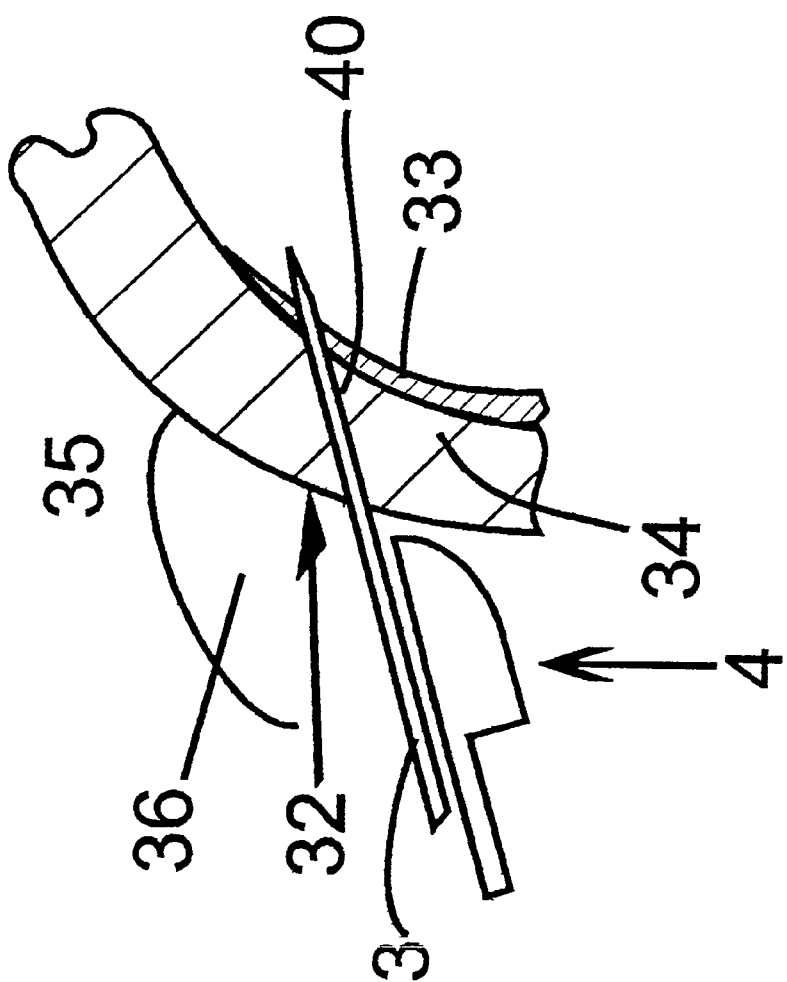
FIG. 15 is a diagrammatic, sectional view showing use of the instrument of FIG. 13 in a first stage of an ab externo operation.
Figure 16:
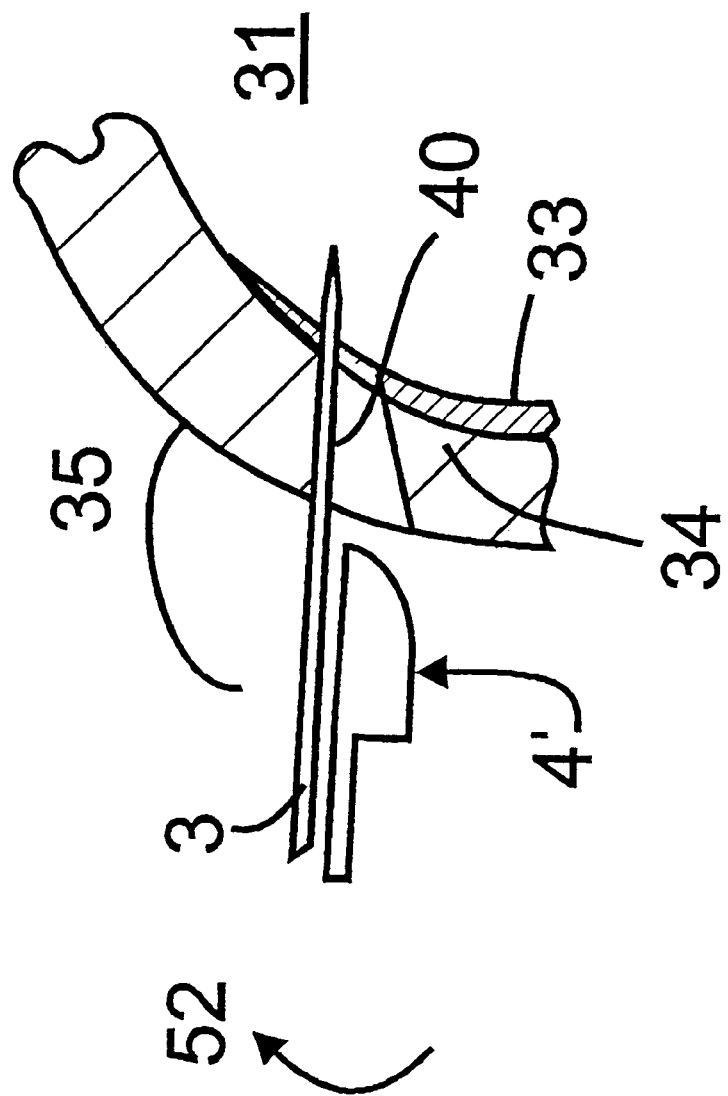
FIG. 16 shows the instrument of FIG. 15 in a second stage of the ab externo operation.
Figure 17:
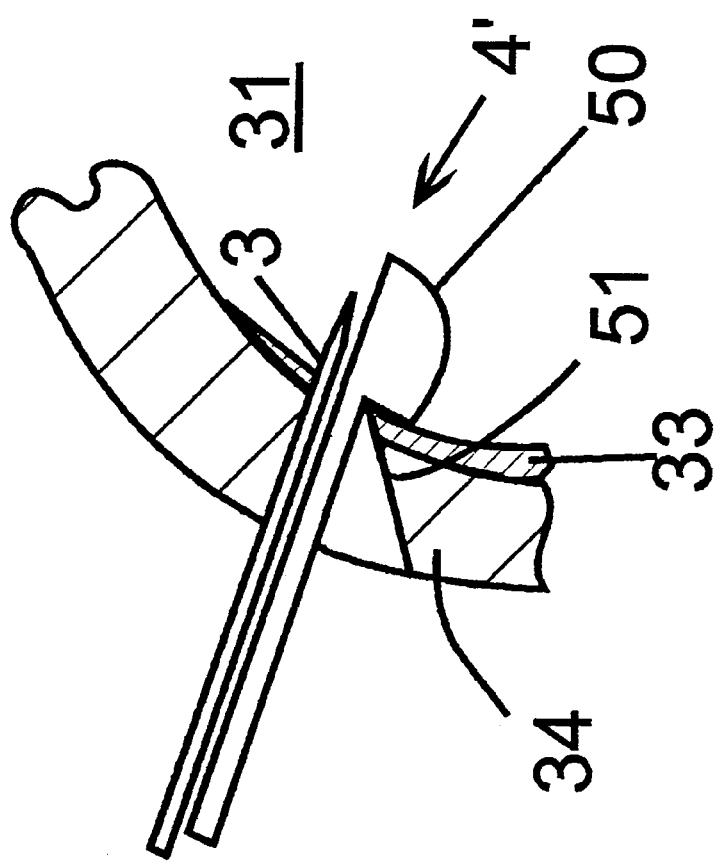
FIG. 17 shows the instrument of FIG. 13 in a third stage of the ab externo operation.
Figure 18:
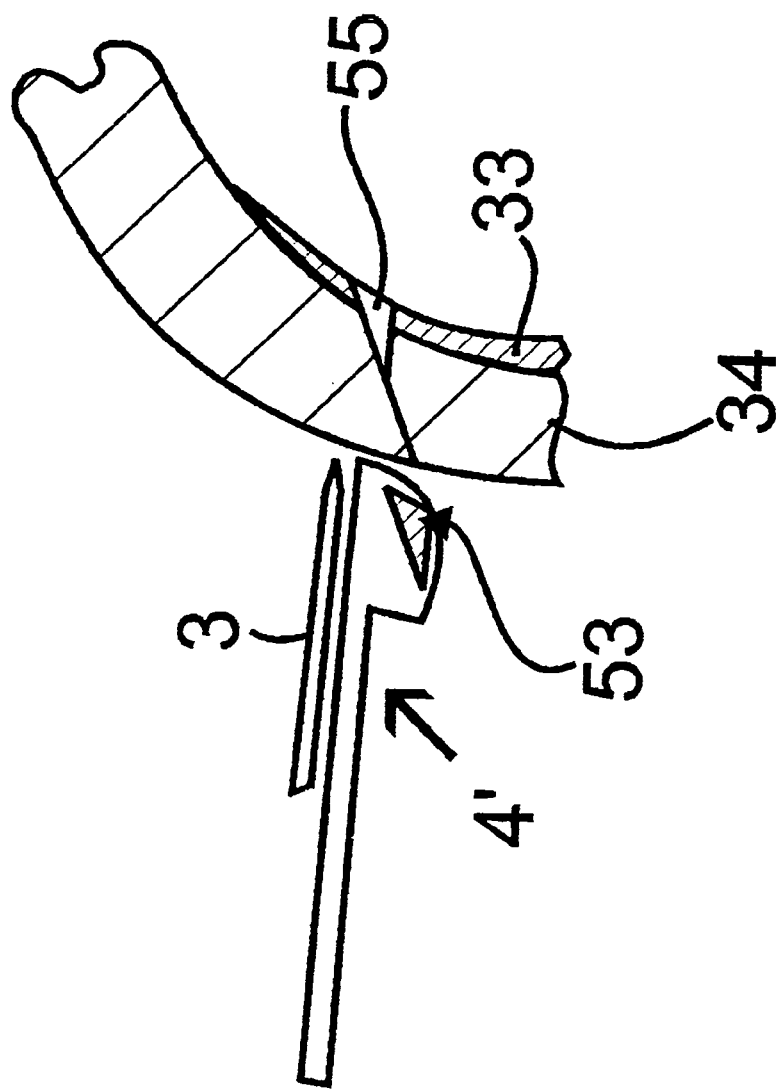
FIG. 18 shows the instrument of FIG. 14 in a fourth stage of the ab externo operation.
Figure 19:
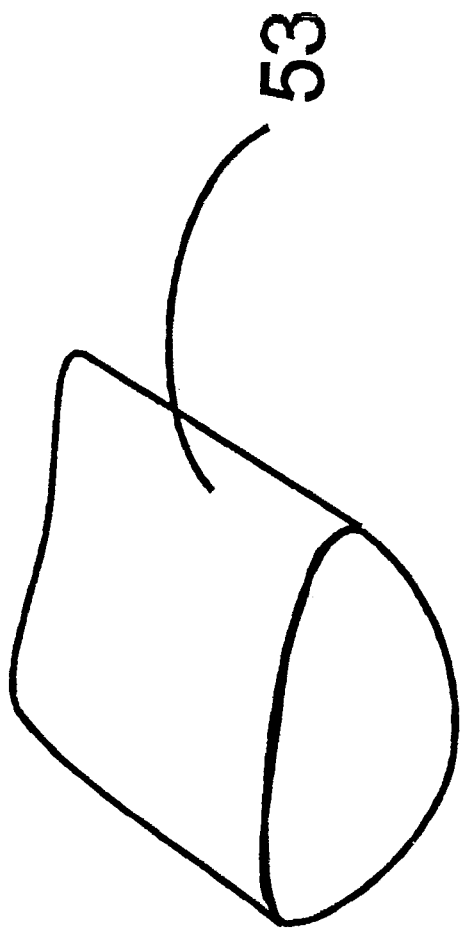
FIG. 19 is a perspective view showing a wedge of tissue excised by the instrument of FIG. 13 in the third stage.

In the ab externo operation shown in FIG. 15, the flat blade 3 is advanced from housing 2' and forms an incision (not shown) in the conjunctiva 36. The instrument is advanced through the incision causing blade 3 to incise the sclera 34 at the level of the trabecular meshwork 33 and form a tunnel 40 in the sclera. The relation to the corneal limbus 35 is shown. The depth of incision is determined by the marking means 24 on blade 3. With blade 3 extending in the incision in the sclera, the entire instrument is then tilted in the direction of arrow 52 (FIG. 16) to enlarge the tunnel 40 and prepare the tissue wall for excision of a segment of the wall proximally of the posterior surface. In this stage, in the case of use of instrument 1 in FIG. 1, the curved blade 4 is advanced to contact the lower surface of flat blade 3 to gouge out a segment of the sclera principally at the trabecular meshwork 33 and excise the segment of the sclera (as in the ab interno operation shown in FIG. 10 but in the reverse direction) whereafter the instrument is then removed to extract the excised segment with the blades. In the embodiment shown in FIG. 13, however, the punch 4' is advanced through the enlarged pocket 40 into the anterior chamber 31 behind the tissue wall so that the cutting edges 51 of punch portion 50 face the anterior surface of the tissue wall as shown in FIG. 17. The punch 4' is then retracted to punch out a wedge-shaped segment 53 (FIG. 18), essentially from the trabecular meshwork 33. The instrument 1', with blade 3 and punch 4' retracted, is then removed from the eye with the segment 53 retained in the punch portion 50. A fistula is formed in the wall by the tunnel 40 and the ostium or opening 55 produced by removal of the segment 53 (FIG. 18). Because the main part of the fistula is obtained by the ostium 55 at the posterior part of the tissue wall 34 the result is colloquially referred to as a partial thickness fistula.

In the ab interno procedure, the operation is reversed and instead of proceeding at the anterior side of the sclera, the instrument proceeds through the anterior chamber to the posterior side of the sclera.

Third Embodiment with Tissue-Cutting Laser Beam

As in the previous embodiments, the same or similar reference numerals will be used to designate the same or similar elements. This embodiment is essentially distinguished from the first two embodiments in that instead of the cutting means formed by the cutting blade or punch, a laser beam is employed. The laser beam can be one which cuts, ablates or removes tissue. Also, instead of incising the entire wall of the sclera, only a partial thickness incision is made as will be seen subsequently.

Figure 20:
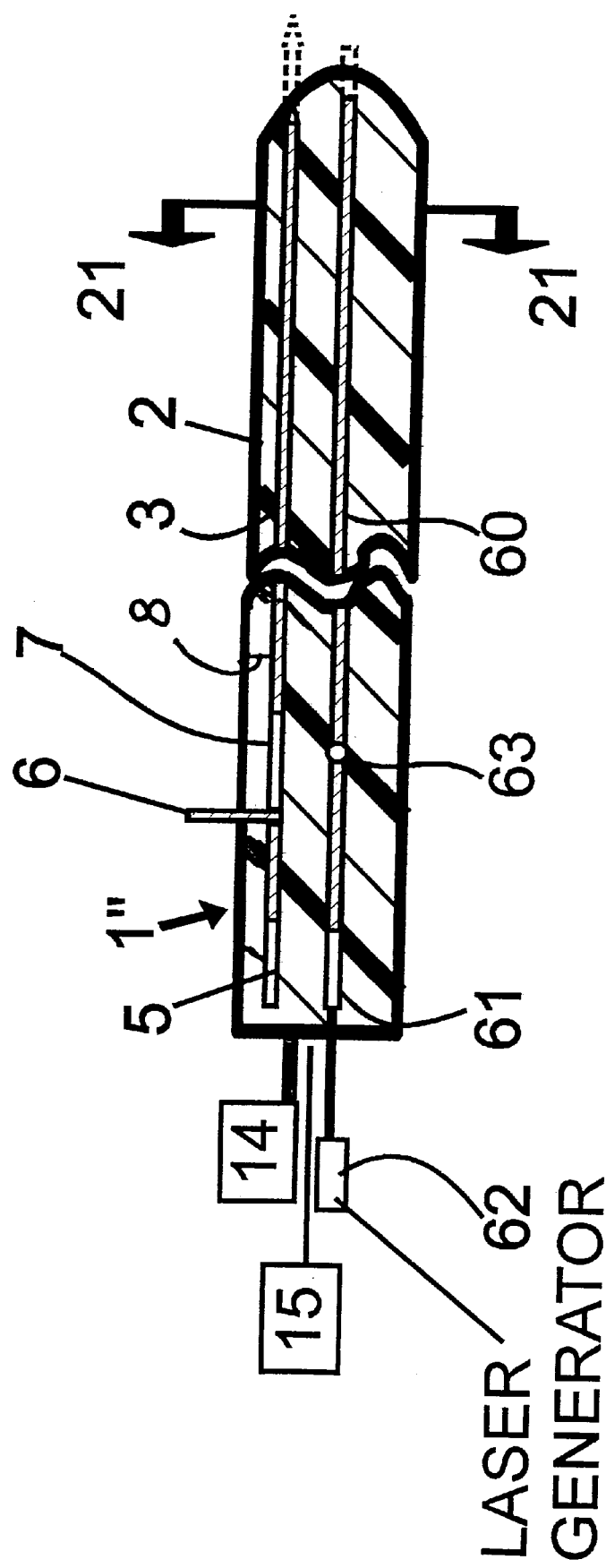
FIG. 20 is a longitudinal, cross-sectional view through a third embodiment of the instrument of the invention.
Figure 21:
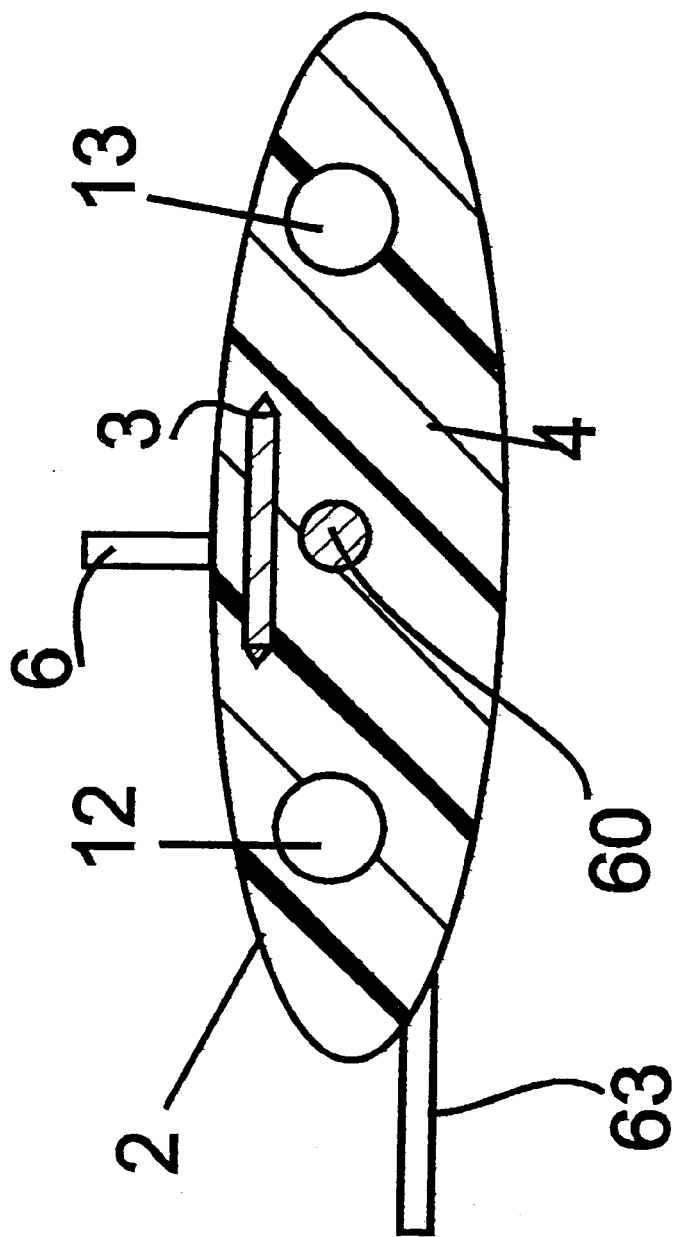
FIG. 21 is a transverse cross-sectional view taken along line 21—21 in FIG. 20.

Referring to FIGS. 20 and 21 therein is seen a probe or instrument 1" whose housing 2" contains slidable flat blade 3. The blade 3 is slidably movable in slot 5 by manually engaging the lever 6. The flat blade 3 is movable between a retracted position shown in solid lines in FIG. 20 and an extended position shown in dotted lines. Instead of the cutting blade or punch of the first two embodiments, an optical fiber 60 for transmitting a laser beam is located in a longitudinal bore 61 in housing 2" beneath blade 3. The optical fiber 60 is connected to a laser generator 62 capable of generating a tissue-cutting laser beam. A lever 63 is secured to the fiber 60 and extends laterally outside the housing through a slot (not shown) in the housing 2" for moving the optical fiber between a retracted, inoperative position as shown in solid lines and an extended, operative position shown in dotted lines. As in the first two embodiments, irrigation channel 12 and aspiration channel 13 are provided in the housing and are respectively connected to irrigation and aspiration sources 14 and 15.

The probe 1" is utilized in much the same manner as the first two embodiments in that the blade 3 makes the initial incision of small size in the tissue wall, whereafter the cutting means formed by the laser generator 62 and optical fiber 60 produces the opening of large size in the partial thickness of the tissue wall, while the blade remains in the initial incision, thereby to complete the formation of the fistula.

Figure 22:
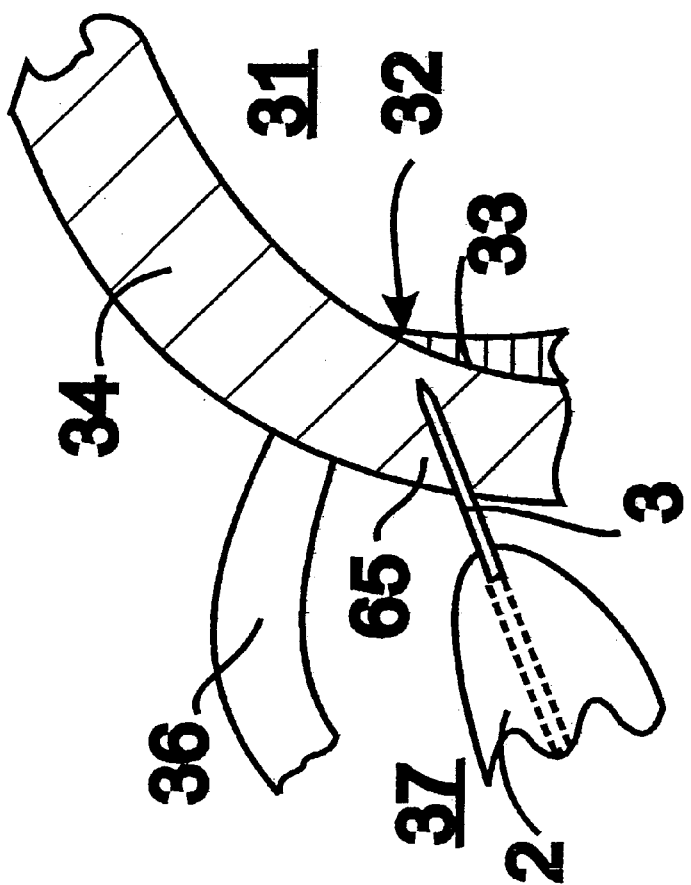
FIG. 22 is a diagrammatic sectional view showing the instrument of FIG. 20 in a first stage of an ab externo operation.
Figure 23:
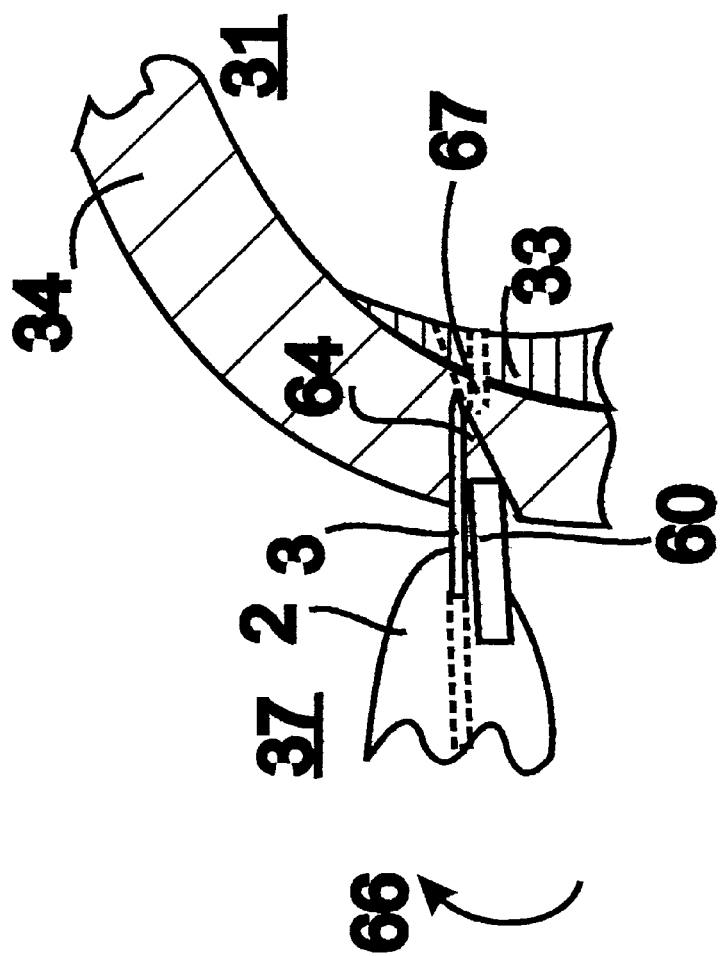
FIG. 23 shows the instrument of FIG. 22 in a further stage of the ab externo operation.
Figure 24:
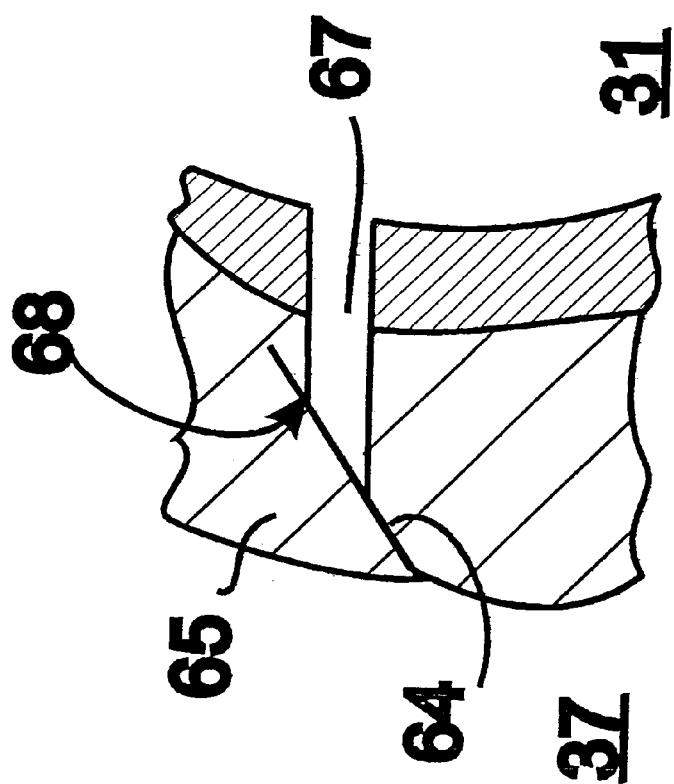
FIG. 24 shows the partial thickness fistula formed by the instrument of FIG. 20.
Figure 25:
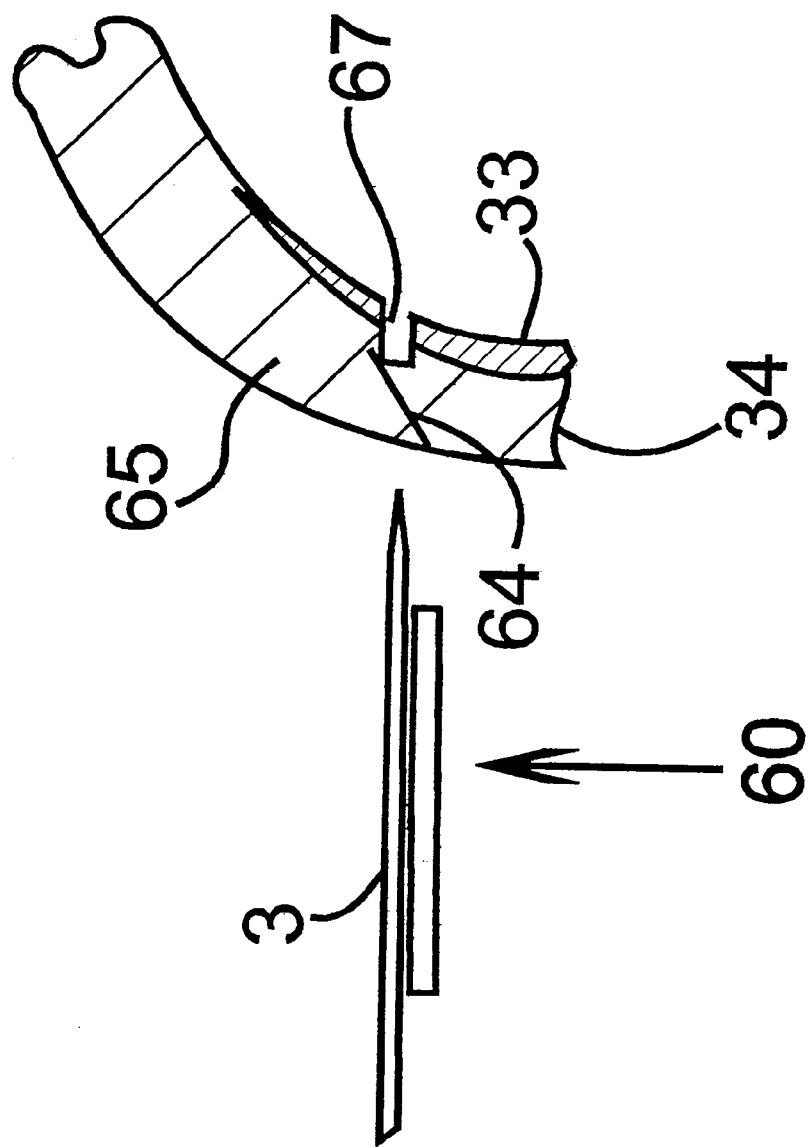
FIGS. 25–29 show successive stages in an ab externo procedure using the first embodiment of the instrument.

Referring to FIG. 22 illustrating the ab externo operation with the probe 1", the extended blade 3 has penetrated through the conjunctiva 36 and penetrated into the sclera 34 of the tissue wall 32 only through a portion of the thickness of wall 32. The side and front edges of the blade 3 are sharp allowing penetration by the blade of the ocular tissues. It is to be noted that prior to penetration of tissue wall 32, the blade 3 has penetrated the conjunctiva 36 without the need for a separate cutting or piercing instrument as in the known art. The blade 3 penetrates into the sclera 34 to a depth indicated by the marking means 24 (see FIG. 4) whereafter the instrument is rocked in opposite directions around the longitudinal axis of the blade so that the side cutting edges of blade 3 form cuts in the superior portion of wall 32 whereby a pocket 64 (FIG. 23) is formed which is surmounted by a flap of tissue 65 (FIG. 24) referred to as a lamellar scleral flap. With the blade 3 in the pocket 64, the instrument is tilted in the direction of arrow 66 as shown in FIG. 23 to enlarge the pocket 64 and position the axis of the optical fiber 60 in facing relation to the sclera 34. The optical fiber 60 is then extended from housing 2" to its operative position in the pocket 64 and the laser generator 62 is activated to produce a large size hole 67 through that portion of the sclera wall 34 and the trabecular meshwork 33 from the point at which the optical fiber 60 faces the bottom surface of the pocket 64 and the posterior surface of tissue wall 32. The blade 3 can be retracted when the optical fiber 60 has been extended into the pocket 64. After the hole 67 has been formed by the laser beam, the instrument 1" is removed leaving a fistula 68 (FIG. 24) composed of the initial slit incision in wall 32 connected to the hole 67. Although the optical fiber has been shown and described as being axially displaceable in the instrument, the optical fiber could also be fixed as the location of the laser beam in the incision can be visualized without extending the optical fiber. The fistula 68 provides an outflow path for controlled flow of aqueous humor from the anterior chamber 31 to the subconjunctival space 37 to reduce pressure in the anterior chamber, the scleral flap 65 modulating the outflow in the manner of a valve.

The operation is carried out in reverse in the ab interno procedure in the manner explained for the first and second embodiments.

First Embodiment in Ab-Externo Procedure

FIGS. 26–29 show the use of the first embodiment of the instrument in the ab externo procedure.

Figure 26:
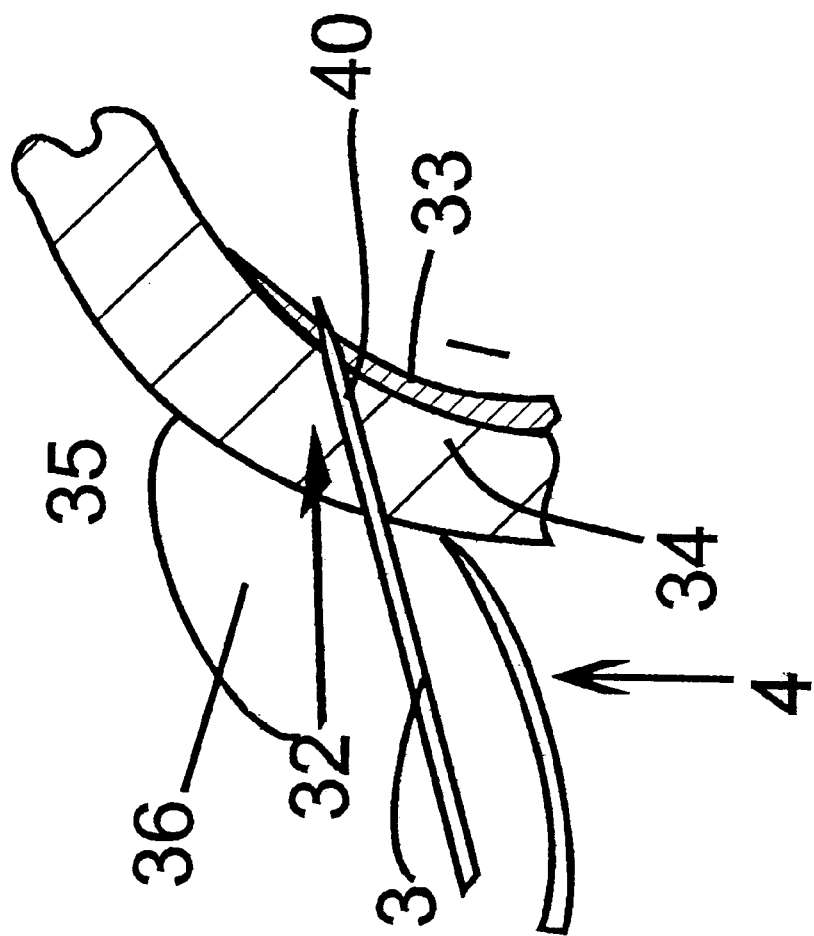
Figure 27:
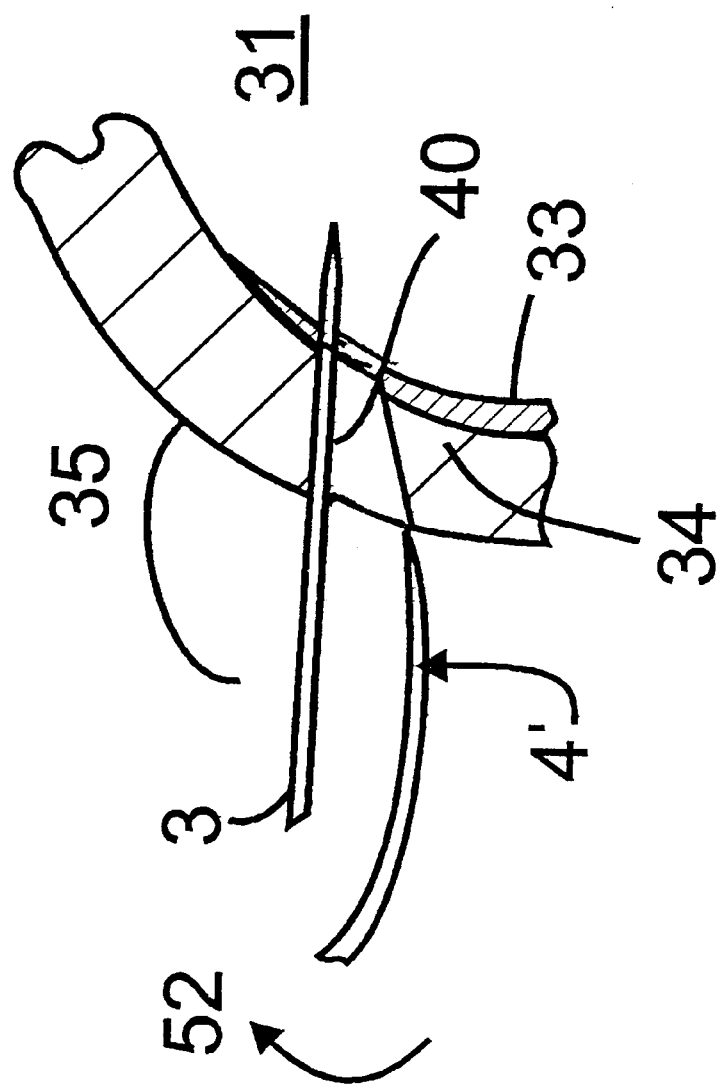
Figure 28:
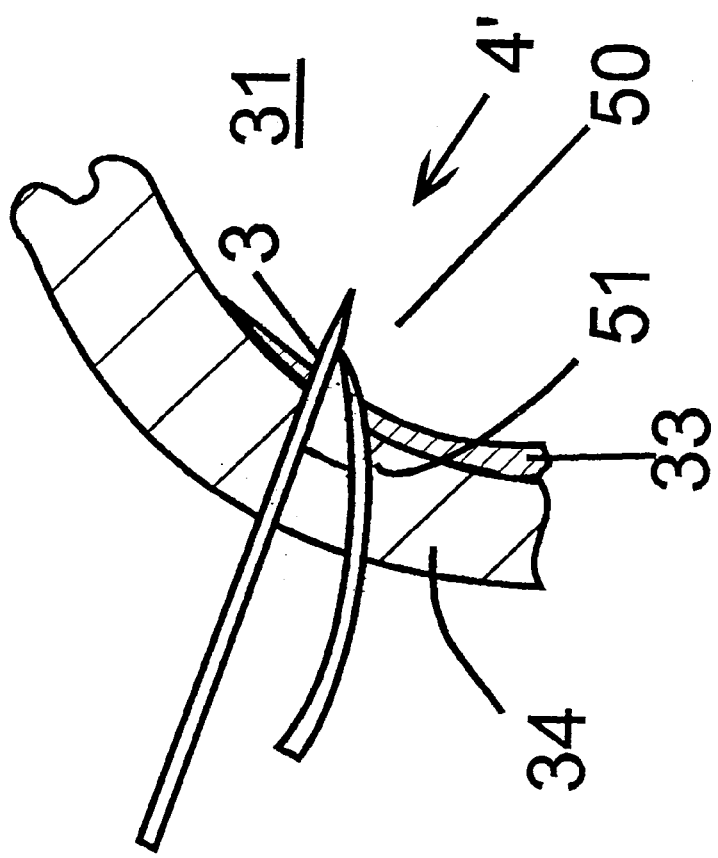
Figure 29:
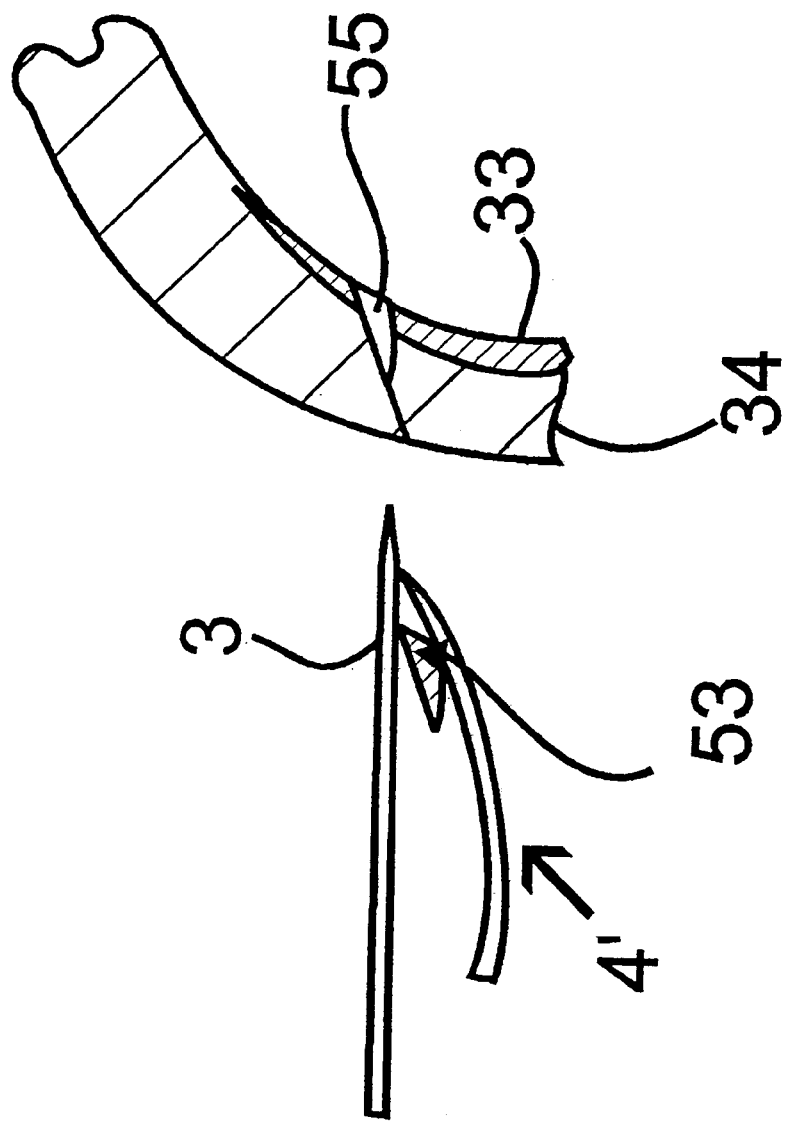

FIG. 26 shows the instrument in the stage in which blade 3 has been extended through the thickness of the tissue wall 32 to form a thin slit in the wall. A lamellar flap can be formed above the slit by partially retracting blade 3 into the wall by an amount to form a flap of desired length after which the blade is rocked to form the flap with one or two free sides as previously explained. The curved blade 4 remains retracted in the housing of the instrument and has not penetrated the tissue wall 32. The blade 3 is then extended to the position shown in FIG. 28 and while the blade 3 remains in the slit, the instrument is tilted and lifted upwardly as shown in FIG. 27 to enlarge the slit opening. The curved blade 4 is then advanced as shown in FIG. 28 to gouge out a segment 53 of the tissue wall. The instrument is then retracted with the blades 3 and 4 remaining extended and holding the segment 53 therein as shown in FIG. 29. A fistula is then formed in the tissue wall by the thin slit produced by blade 3 and a large size ostium 55 produced by removal of segment 53 by blade 4.

In order to permit removal of the blades for cleaning, sharpening or replacement, the actuating levers 6, 11 are separable from the respective blades, for example, by providing a threaded engagement therebetween. In order to remove a blade, it is displaced to an extended position and the associated lever is unscrewed from the blade whereafter the blade is removable at the front of the instrument. Replacement is carried out in reverse order. In a further embodiment, the blades and the fluid channels are supported in a sleeve separably connected in the housing, so that different sizes and shapes of blades can be readily utilized depending on conditions of the particular patient.

Although the invention has been described in relation to specific embodiments thereof, it will become apparent to those skilled in the art that numerous modifications and variations can be made within the scope and spirit of the invention as defined in the attached claims.

What is claimed is:

1. An instrument for producing a fistula in a tissue wall of an eye of a patient, said tissue wall having anterior and posterior surfaces, said instrument comprising a housing, a flat blade supported in said housing for movement in its plane for extending from the housing to penetrate the tissue wall of a patient and produce an incised slit in said tissue wall extending through said wall and said anterior and posterior surfaces to form an opening extending through said wall, and tissue excising means carried by said housing, said flat blade being so supported in said housing to lift an upper edge of said slit away from a lower edge of said slit and widen said opening in said tissue wall when said housing is tilted, said tissue excising means being positioned in said housing to enter into said opening, while said flat blade remains in said slit and widens said opening, for excising tissue from only a portion of the thickness of said wall at said lower edge of the slit to said posterior surface, to produce an aperture in said portion of the thickness of said tissue wall to form a fistula in said tissue wall constituted in part by said slit and in part by said aperture joined to said slit, said means for excising tissue comprising a second blade movable in said housing relative to the first said blade to enter said opening while said flat blade remains in said opening, said second blade being shaped to form said aperture by excising tissue from said portion of said wall, and upon removal of said housing from said opening, the excised tissue is removed.

2. An instrument as claimed in claim 1, wherein said housing is provided with channels for respective irrigation and aspiration of a fluid.

3. An instrument as claimed in claim 1, comprising means accessible from outside said housing for moving said blade between an extended position from said housing and a retracted position in said housing.

4. An instrument as claimed in claim 3, wherein said means for moving said blade comprises a manually operable lever connected to said blade and extending externally from said housing.

5. An instrument as claimed in claim 1, wherein said second blade is a scoop-shaped blade having exposed cutting edges, said second blade being guided for movement in said housing for travel along a curved path in which a forward end of said second blade approaches said flat blade at an angle to form a wedge-shaped space therewith to cut said tissue from said portion of the tissue wall.

6. An instrument as claimed in claim 1, wherein said second blade comprises a hollow punch.

7. An instrument as claimed in claim 6, wherein said punch has rearwardly facing cutting edges.

8. An instrument as claimed in claim 6, wherein said punch is supported in said housing for movement substantially parallel to said first blade.

9. An instrument as claimed in claim 1, wherein said first and second blades are removable from said housing.

10. An instrument as claimed in claim 1, wherein said tissue excising means is positioned relative to said blade and is constructed and arranged to produce said aperture from an intermediate location along the lower edge of the slit to said posterior surface of said wall.

11. An instrument as claimed in claim 10, wherein the tissue wall is the sclera of an eye, said tissue excising means forming said aperture with a substantially greater size than said slit.

12. An instrument as claimed in claim 1, wherein said flat blade has a front cutting edge and lateral cutting edges so that said first cutting edge forms said slit while said lateral cutting edges form a flap at said anterior surface of said wall.

13. An instrument for producing a fistula in a tissue wall of an eye of a patient, said tissue wall having anterior and posterior surfaces, said instrument comprising a housing which is longitudinally elongated, a flat blade supported in said housing and extending longitudinally from the housing to penetrate the tissue wall of a patient and produce an incised slit in said tissue wall extending through said wall and said anterior and posterior surfaces to form an opening extending completely through said wall, and tissue excising means supported by said housing, said flat blade being in a superior position in said housing and said tissue excising means being in an inferior position in said housing, said housing being manually engageable to tilt said housing while said flat blade is inserted in said slit to lift an upper edge of said slit away from a lower edge of said slit and widen said opening in said tissue wall, said tissue excising means being so positioned in said housing relative to said flat blade to face the widened opening while said blade lifts the upper edge of said slit, for excising tissue from only a portion of the thickness of said wall at said lower edge of the slit to said posterior surface, to produce an aperture only in said portion of the thickness of said tissue wall and form a fistula in said tissue wall constituted in part by said slit and in part by said aperture joined to said slit, said tissue excising means comprising a tissue removal device constructed and arranged so that said aperture which is produced by said tissue excising means is substantially greater in size than said slit and forms the main part of said fistula.

14. An instrument as claimed in claim 13, wherein said flat blade is supported for movement in said housing in a plane containing said blade.

15. An instrument as claimed in claim 13, wherein said tissue removal device comprises laser generating means for producing a tissue-cutting laser beam.

16. An instrument as claimed in claim 15, wherein said laser generating means comprises an optical fiber in said housing extending adjacent to said blade.

17. An instrument as claimed in claim 13, wherein said tissue removal device comprises a curved blade.

18. An instrument as claimed in claim 13, wherein said tissue removal device comprises a hollow punch.

19. An instrument as claimed in claim 13, wherein said flat blade is secured against rotation in said housing in a position offset with respect to a longitudinal axis of said housing.

\* \* \* \* \*